United States Patent
Leroy et al.

(10) Patent No.: US 8,962,837 B2
(45) Date of Patent: Feb. 24, 2015

(54) NITROGEN HETEROCYCLE DERIVATIVES, PREPARATION THEREOF AND APPLICATION THEREOF IN HUMAN THERAPEUTICS

(75) Inventors: Isabelle Leroy, Frouzins (FR); Elisabeth Dupont-Passelaigue, Colomiers (FR); Samuel Mialhe, Castres (FR); Didier Junquero, Castres (FR); Karine Valeille, Palaiseau (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 0 days.

(21) Appl. No.: 13/642,025

(22) PCT Filed: Apr. 15, 2011

(86) PCT No.: PCT/EP2011/056066
§ 371 (c)(1),
(2), (4) Date: Oct. 18, 2012

(87) PCT Pub. No.: WO2011/131593
PCT Pub. Date: Oct. 27, 2011

(65) Prior Publication Data
US 2013/0040928 A1    Feb. 14, 2013

(30) Foreign Application Priority Data
Apr. 19, 2010  (FR) .................................... 10 52943

(51) Int. Cl.
*C07D 403/04*  (2006.01)
*A61K 31/497*  (2006.01)
*C07D 241/18*  (2006.01)
*C07D 253/07*  (2006.01)

(52) U.S. Cl.
CPC ............ *C07D 241/18* (2013.01); *C07D 253/07* (2013.01)
USPC ...................... 544/408; 514/255.05

(58) Field of Classification Search
CPC ................................................... C07D 403/04
See application file for complete search history.

(56) References Cited

U.S. PATENT DOCUMENTS

2008/0280916 A1   11/2008  Bilich et al.
2011/0118266 A1    5/2011  Leroy et al.

FOREIGN PATENT DOCUMENTS

| FR |      2933979 A1 | 1/2010 |
| WO | WO 2008/046226 A1 | 4/2008 |
| WO | WO 2008/089580 A1 | 7/2008 |
| WO | WO 2009/019566 A1 | 2/2009 |
| WO | WO 2010/006962 A1 | 1/2010 |

OTHER PUBLICATIONS

Liu et al.; Stearoyl CoA Desaturase 1: Role in Cellular Inflammation and Stress; 2011; American Society for Nutrition. Adv. Nutr. 2: 15-22.*
Flowers et al.; "Metabolic Changes in Skin Caused by Scd1 Deficiency: A Focus on Retinol Metabolism"; PLoS ONE 6(5): e19734. doi:10.1371/journal.pone.0019734; pp. 1-18.*
Hartz, et al.; "In Vitro Intrinsic Clearance-Based Optimization of N3-Phenylpyrazinones as Corticotropin-Releasing Factor-1 (CRF1) Receptor Antagonists."; 2009; J. Med. Chem.; 52: 4161-4172.*
Attie et al., "Relationship between stearoyl-CoA desaturase activity and plasma triglycerides in human and mouse hypertriglyceridemia," Journal of Lipid Research, vol. 43, 2002, pp. 1899-1907.
Biddinger et al., "Leptin Suppresses Stearoyl-CoA Desaturase 1 by Mechanisms Independent of Insulin and Sterol Regulatory Element-Binding Protein-1c," Diabetes, vol. 55, Jul. 2006, pp. 2032-2041.

(Continued)

*Primary Examiner* — Timothy Thomas
(74) *Attorney, Agent, or Firm* — Birch, Stewart, Kolasch & Birch, LLP

(57) ABSTRACT

The present invention relates to compounds having general formula I characterized in that

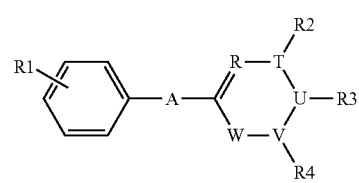

wherein in particular:
$R_1$ represents one or a plurality of groups such as: trifluoromethyl, halogen such as F, Cl, Br, methyl, nitro.
R represents nitrogen
T-U represents C=C, V represents N, W represents C=O, $R_2$ represents Cl or H, $R_3$=H and $R_4$=Me,
A represents

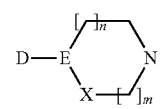

wherein n=m=1, X represents —$CH_2$— and E represents —CH—, and D represents oxygen,
along with the various isomers and mixtures thereof in any proportions, and the pharmaceutically acceptable salts thereof.

7 Claims, No Drawings

(56) References Cited

OTHER PUBLICATIONS

Cohen et al., "Role for Stearoyl-CoA Desaturase-1 in Leptin-Mediated Weight Loss," Science, vol. 297, Jul. 12, 2002, pp. 240-243.

Dobrzyn et al., "Stearoyl-CoA desaturase as a new drug target for obesity treatment," The International Association for the Study of Obesity, Obesity reviews, vol. 6, pp. 169-174, 2005.

Falvella et al., "Stearoyl-CoA desaturase 1 (Scd1) gene overexpression is associated with genetic predisposition to hepatocarcinogenesis in mice and rats," Carcinogenesis, vol. 23, No. 11, 2002, pp. 1933-1936.

File Chemcats "Ambinter Stock Screening Collection," Accession No. 0006581746, Feb. 8, 2010, 1 page, XP002599128.

Fritz et al., "Abrogation of De novo Lipogenesis by Stearoyl-CoA Desaturase 1 Inhibition Interferes with Oncogenic Signaling and Blocks Prostate Cancer Progression in Mice," Molecular Cancer Therapeutics, vol. 9, No. 6, Jun. 2010 (First published online: Jun. 8, 2010), pp. 1740-1754.

Harrison et al., "Expression of Lipogenic Factors Galectin-12, Resistin, SREBP-1, and SCD in Human Sebaceous Glands and Cultured Sebocytes," Journal of Investigative Dermatology, vol. 127, 2007 (published online: Match 15, 2007), pp. 1309-1317.

Hulver et al., "Elevated stearoyl-CoA desaturase-1 expression in skeletal muscle contributes to abnormal fatty acid partitioning in obese humans," Cell Metabolism, vol. 2 Oct. 2005, pp. 251-261.

International Search Report dated Jul. 1, 2011 for International Application No. PCT/EP2011/056066.

Miyazaki et al., "A lipogenic diet in mice with a disruption of the stearoyl-CoA desaturase-1 gene reveals a stringent requirement of endogenous monounsaturated fatty acids for triglyceride synthesis" Journal of Lipid Research, vol. 42, 2001, pp. 1018-1024.

Ntambi et al., "Loss of Stearoyl-CoA desaturase-1 function protects mice against adiposity," PNAS, vol. 99, No. 17, Aug. 20, 2002, pp. 11482-11486.

Okada et al., "Plasma palmitoleic acid content and obesity in children," The American Journal of Clinical Nutrition, vol. 82, 2005, pp. 747-750.

Scaglia et al., "Inhibition of Stearoyl-CoA Desaturase 1 expression in human lung adenocarcinoma cells impairs tumorigenesis," International Journal of Oncology, vol. 33, 2008, pp. 839-850.

Scaglia et al., "Inhibition of StearoylCoA Desaturase-1 Inactivates Acetyl-CoA Carboxylase and Impairs Proliferation in Cancer Cells: Role of AMPK," PLoS ONE, vol. 4, Issue 8, e6812, Aug. 2009, pp. 1-14.

Scaglia et al., "Stearoyl-CoA Desaturase is Involved in the Control of Proliferation, Anchorage-independent Growth, and Survival in Human Transformed Cells," J. Biol. Chem., vol. 280, No. 27, Jul. 8, 2005, pp. 25339-25349.

Sundberg et al., "Asebia-2J (Scd1ab2J): A New Allele and a Model for Scarring Alopecia," American Journal of Pathology, vol. 156, No. 6, Jun. 2000, pp. 2067-2075.

Zheng et al., "Scd1 is expressed in sebaceous glands and is disrupted in the asebia mouse," Nature Genetics, vol. 23, Nov. 1999, pp. 268-270.

\* cited by examiner

NITROGEN HETEROCYCLE DERIVATIVES, PREPARATION THEREOF AND APPLICATION THEREOF IN HUMAN THERAPEUTICS

The present invention relates to nitrogen heterocycle derivatives inhibiting SCD-1 enzyme activity and the application thereof in human therapeutics.

Stearoyl-CoA Desaturase-1 (SCD-1), also referred to as Δ9-desaturase, is an enzyme limiting monounsaturated fatty acid synthesis under the control of the transcription factor SREBP$_{1C}$ (Miyazaki, M., Kim, Y. C., Ntambi, J. M. A lipogenic diet in mice with a disruption of the stearoyl-CoA desaturase-1 gene reveals a stringent requirement of endogenous monounsaturated fatty acids for triglyceride synthesis. J Lipid Res 42, 1018-1024 (2001)). These monounsaturated fatty acids are involved in the biosynthesis of phospholipids, triglycerides, cholesterol esters and wax esters (Dobrzyn, A.; Ntambi, J. M. Stearoyl-CoA desaturase as a new drug target for obesity treatment. Obesity reviews, 6, 169-174 (2005)).

SCD-1 gene invalidation in mice renders mice resistant to genetic or diet-induced obesity; the peripheral effects of leptin on increased energy expenditure, weight loss and insulin sensitivity are inversely correlated with SCD-1 gene expression and enzyme activity (Cohen, P., Miyazaki, M., Socci, N. D. et al. Role for stearoyl-CoA desaturase-1 in leptin-mediated weight loss. Science 297, 240-243 (2002), Ntambi, J. M., Miyazaki, M., Stoehr, J. P. et al. Loss of stearoyl-CoA desaturase-1 function protects mice against adiposity. Proc Natl Acad Sci 99, 11482-11486 (2002), Biddinger, S. B., Miyazaki, M., Boucher, J. et al. Leptin suppresses stearoyl-CoA desaturase-1 by mechanisms independent of insulin and sterol regulatory element-binding protein-1c. Diabetes 55, 2032-2041 (2006)).

The role of SCD-1 in the pathogenecity of obesity is supported by the correlation between the plasma palmitoleic acid concentration and abdominal adiposity in children. (Okada, T., Furuhashi, N., Kuromori, Y. et al. Plasma palmitoleic acid content and obesity in children. Am J Clin Nutr 82, 747-750 (2005)), along with the association of SCD-1 overexpression in the skeletal muscle in obese adults with poor fatty acid partitioning inducing liver 1-oxidation inhibition (Hulver, M. W., Berggren, J. R., Carper, M. J. et al. Elevated stearoyl-CoA desaturase-1 expression in skeletal muscle contributes to abnormal fatty acid partitioning in obese humans. Cell Metab 2, 251-261 (2005)). The plasma ratio 18:1/18:0, also referred to as the "desaturation index", is emerging as the biomarker of SCD-1 in humans and correlates with the plasma triglyceride level and in an inversely proportional manner with the HDL level (Attie, A. D., Krauss, R. M., Gray-Keller, M. P. et al. Relationship between stearoyl-CoA desaturase activity and plasma triglycerides in human and mouse hypertriglyceridemia. J Lipid Res 43, 1899-1907 (2002)).

Moreover, SCD1 and the lipogenesis pathway are expressed in human sebaceous glands (Harrison, W. J., Bull, J. J., Seltmann, H. et al. Expression of lipogenic factors Galectin-12, Resistin, SREBP-1, and SCD in human sebaceous glands and cultures sebocytes. J Invest Dermatol 127, 1309-1317 (2007)) and in mice. Mice in which the SCD-1 gene is mutated (Asebia) or invalidated ("knock-out") exhibit sebaceous gland atrophy (Cohen, P., Miyazaki, M., Socci, N. D. et al. Role for stearoyl-CoA desaturase-1 in leptin-mediated weight loss. Science 297, 240-243 (2002), Zheng, Y., Eilertsen, K. J., Ge, L. et al. SCD1 is expressed in sebaceous glands and is disrupted in the asebia mouse. Nat Genet. 23, 268-270 (1999), Sundberg, J. P., Boggess, D., Sundberg, B. A. et al. Asebia-2J (Scd1ab2j): a new allele and model for scaring alopecia. Am J Pathol 156, 2067-2075 (2000)).

The benefit of the SCD-1 target in dermatology is supported by the fact that hyper-seborrhoea is an essential factor involved in the physiopathology of acne. This reasoning is supported by the recent claim of SCD-1 inhibitors in dermatology with respect to indications such as acne, rosacea or hyperseborrhoea (US2008280916) and sebum production inhibition (WO2009019566).

The role of SCD1 in oncology is suggested by the predisposition in rodents (mice, rats) to specific genetic backgrounds displaying high SCD1 expression (increased 4 to 10-fold) associated with hepatocarcinogenesis, on one hand (Falvella, F. S., Pascale, R. M., Gariboldi, M. et al. Stearoyl-CoA desaturase (Scd1) gene overexpression is associated with genetic predisposition to hepatocarcinogenesis in mice and rats. Carcinogenesis 23, 1933-1936 (2002)), and by the role of monounsaturated fatty acids produced by SCD1 in cancerous line proliferation and invasion capacity, on the other (Scaglia, N. and Igal, R. A. Stearoyl-CoA desaturase is involved in the control of proliferation, anchorage-independent growth, and survival in human transformed cells. J Biol Chem 280, 25339-25349 (2005)). Conversely, invalidation of SCD1 expression ("knock-down") with an antisense strategy reduces proliferation, stimulates apoptosis and prevents in vitro and in vivo lung adenocarcinoma cell invasion, demonstrating the benefit of SCD1 inhibition as an anticancer target (Scaglia, N. and Igal, R. A. Inhibition of stearoyl-CoA desaturase 1 expression in human lung adenocarcinoma cells impairs tumorigenesis. Int J Oncol 33, 839-850 (2008)). Furthermore, de novo lipogenesis inactivation by chemical SCD1 inhibitors (pharmacological intervention) confirms the relevance of this strategy (Scaglia, N., Chisholm, J. W., Igal, R. A. Inhibition of stearoylCoA desaturase-1 inactivates acetyl-CoA carboxylase and impairs proliferation in cancer cells: role of AMPK. PLoS one 4, e6812-1-13 (2009); Fritz, V., Benfodda, Z., Rodier, G. et al. Abrogation of de novo lipogenesis by stearoyl-CoA desaturase 1 inhibition interferes with oncogenic signaling and blocks prostate cancer progression in mice. Mol Cancer Ther 9, 1740-1754 (2010)).

Consequently, SCD-1 inhibition is emerging as a therapeutic target of choice in the treatment of obesity, type 2 diabetes and lipid disorders associated with metabolic syndrome and for the treatment of cancer and also in dermatology in skin-related lipid disorders.

We have previously described compounds inhibiting SCD-1 enzyme activity (FR2933979/WO2010006962). However, modifying the termination revealed, unexpectedly, stronger compounds. The present invention relates to these nitrogen heterocycle derivatives inhibiting SCD-1 activity, the preparation thereof and application thereof in human therapeutics.

These compounds corresponding to the general formula I:

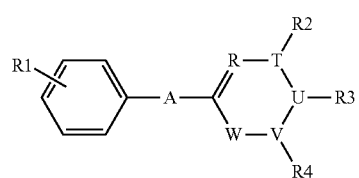

wherein

R$_1$ represents one or a plurality of groups such as: trifluoromethyl, halogen such as F, Cl, Br, nitro, C$_1$-C$_4$ linear or branched alkyl, trifluoromethoxy, acetyl.

A represents

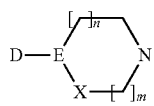

wherein if n=m=1, X represents —CH$_2$— or —CHMe-,
   E represents —CH—, and D represents oxygen or —NH—,
   or E represents nitrogen, and D represents C=O or —CH$_2$—
if n=m=0, X represents —CH$_2$— and E represents —CH—, D represents —OCH$_2$—,
if n=1 and m=0, X represents —CH$_2$— and E represents —CH—, D represents oxygen,
or A represents

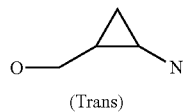

(Trans)

R represents nitrogen
T-U represents C=C, V represents N, W represents C=O, R$_2$ represents Br, Cl or H, R$_3$=H and R$_4$ represents a C$_1$-C$_7$ linear or branched alkyl or alkenyl radical (in this case, the C=R-T-U—V—W heterocycle represents a pyrazin-2-one),
or, T-U represents N=C, V—W represents C=N, R$_2$ does not represent a substituent, (in this case, the heterocycle C=R-T-U—V—W represents a [1,2,4]triazine)
   where R$_3$=H and R$_4$ represents hydrogen or a methyl or a phenyl, optionally substituted by one or a plurality of groups such as trifluoromethyl, OMe, methyl or halogen such as F, Cl, Br excluding the compounds 3-[4-(3-fluoro-benzyl)-piperazin-1-yl]-5-(4-trifluoromethyl-phenyl)-[1,2,4]triazine, 3-[4-(3-Chlorophenoxy)-piperidin-1-yl]-5-(4-fluoro-phenyl)-[1,2,4]triazine, 3-[4-(4-fluoro-phenoxy)-piperidin-1-yl]-5-(4-fluoro-phenyl)-[1,2,4]triazine, 5-(2,6-Dimethoxy-phenyl)-3-(4-m-tolyloxy-piperidin-1-yl)-[1,2,4]triazine,
   or R$_3$=Me and R$_4$ represents hydrogen or a methyl or a phenyl, optionally substituted by one or a plurality of groups such as trifluoromethyl, OMe, halogen such as F, Cl, Br or methyl,
   or R$^3$ and R$_4$ simultaneously represent phenyl or furan or pyridyl,
   or R$_3$ and R$_4$ represent —(CH$_2$)$_4$—
or R represents C
T-U represents C=N, V represents N, W represents C=O, R$_2$=H, R$_3$ does not represent a substituent and R$_4$ represents a C$_1$-C$_7$ linear or branched alkyl or alkenyl radical (in this case, the heterocycle C=R-T-U—V—W represents a 2H-pyridazin-3-one substituted in 4),
or TR$_2$ represents C=O, U represents N, R$_3$ represents a C$_1$-C$_7$ linear or branched alkyl or alkenyl radical, V—W represents N=CH, R$_4$ does not represent a substituent (in this case, the heterocycle C—R-T-U—V—W represents a 2H-pyridazin-3-one substituted in 5).

along with the various isomers and mixtures thereof in any proportions, and the pharmaceutically acceptable salts thereof.

According to one embodiment of the invention, the compounds having the general formula I are those wherein:

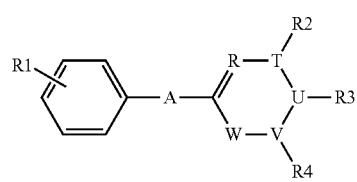

R$_1$ represents one or a plurality of groups such as: trifluoromethyl, halogen such as F, Cl, Br, methyl, nitro.

R represents nitrogen
T-U represents C=C, V represents N, W represents C=O, R$_2$ represents Cl or H, R$_3$=H and R$_4$=Me,
or, T-U represents N=C, V—W represents C=N, R$_2$ does not represent a substituent,
   where R$_3$=H and R$_4$ represents hydrogen or a methyl or a phenyl,
   or R$_3$=Me and then R$_4$ represents hydrogen or a methyl or a phenyl optionally substituted by a trifluoromethyl group,
   or R$_3$ and R$_4$ simultaneously represent phenyl or furan or pyridyl,
   or R$_3$ and R$_4$ represent —(CH$_2$)$_4$—
A represents

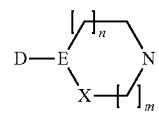

wherein
if n=m=1, X represents —CH$_2$— or —CHMe-,
   E represents —CH—, D represents oxygen or —NH—,
   or E represents nitrogen, D represents C=O or —CH$_2$—.
if n=m=0, X represents —CH$_2$— and E represents —CH—, D represents —OCH$_2$—,
if n=1 and m=0, X represents —CH$_2$— and E represents —CH—, D represents oxygen,
or A represents

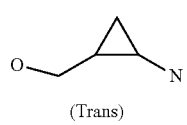

(Trans)

or R represents C
T-U represents C=N, V represents N, W represents C=O, R$_2$=H, R$_3$ does not represent a substituent and R$_4$=Me, in this case, A represents

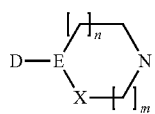

wherein
if n=m=1, X represents —CH$_2$— or —CHMe-,
E represents —CH—, D represents oxygen or —NH—, or E represents nitrogen, D represents C═O or —CH$_2$—.
n=m=0, X represents —CH$_2$— and E represents —CH—, D represents —OCH$_2$—,
if n=1 and m=0, X represents —CH$_2$— and E represents —CH—, D represents oxygen,
or A represents

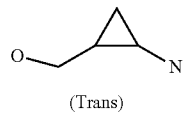

(Trans)

or TR$_2$ represents C═O, U represents N, R$_3$=Me, V—W represents N═CH, R$_4$ does not represent a substituent. in this case, A represents

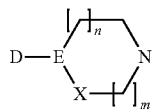

wherein
if n=m=1, X represents —CH$_2$— or —CHMe-, E represents —CH, D represents oxygen,
if n=m=0, X represents —CH$_2$— and E represents —CH—, D represents —OCH$_2$—,
if n=1 and m=0, X represents —CH$_2$— and E represents —CH—, D represents oxygen,
or A represents

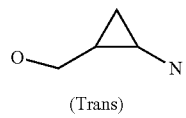

(Trans)

along with the various isomers and mixtures thereof in any proportions, and the pharmaceutically acceptable salts thereof.
According to a further embodiment of the invention, the compounds having the general formula I are those wherein:

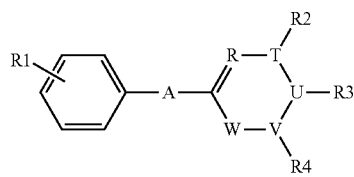

I

R$_1$ represents one or a plurality of groups such as: trifluoromethyl, halogen such as F, Cl, Br, methyl, nitro.
R represents nitrogen
T-U represents C═C, V represents N, W represents C═O, R$_2$ represents Cl or H, R$_3$=H and R$_4$=Me,
or, T-U represents N═C, V—W represents C═N, R$_2$ does not represent a substituent,
  where R$_3$=H and R$_4$ represents hydrogen or a methyl or a phenyl,
  or R$_3$=Me and R$_4$ represents hydrogen or a methyl or a phenyl optionally substituted by a trifluoromethyl group,
  or R$_3$ and R$_4$ simultaneously represent phenyl or furan or pyridyl,
  or R$_3$ and R$_4$ represent —(CH$_2$)$_4$—
A represents

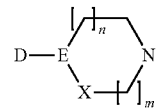

wherein
if n=m=1, X represents —CH$_2$— or —CHMe-,
  E represents CH, D represents oxygen or —NH—,
  or E represents nitrogen, D represents C═O or —CH$_2$—.
if n=m=0, X represents —CH$_2$— and E represents —CH—, D represents —OCH$_2$—,
if n=1 and m=0, X represents —CH$_2$— and E represents —CH—, D represents oxygen,
or R represents C
T-U represents C═N, V represents N, W represents C═O, R$_2$=H, R$_3$ does not represent a substituent and R$_4$=Me,
  in this case, A represents

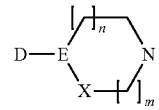

wherein:
if n=m=1, X represents —CH$_2$— or —CHMe-,
  E represents —CH—, D represents oxygen or —NH—,
  or E represents nitrogen, D represents C═O or —CH$_2$—.
if n=m=0, X represents —CH$_2$— and E represents —CH—, D represents —OCH$_2$—,
if n=1 and m=0, X represents —CH$_2$— and E represents —CH—, D represents oxygen,
along with the various isomers and mixtures thereof in any proportions, and the pharmaceutically acceptable salts thereof.
According to a further embodiment of the invention, the compounds having general formula I are those wherein:

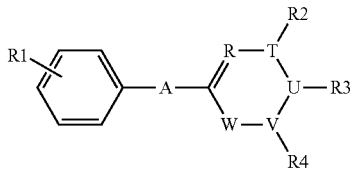

R₁ represents one or a plurality of groups such as: trifluoromethyl, halogen such as F, Cl, Br, methyl, nitro.
R represents nitrogen
T-U represents C=C, V represents N, W represents C=O, R₂ represents Cl or H, R₃=H and R₄=Me,
or, T-U represents N=C, V—W represents C=N, R₂ does not represent a substituent,
where R₃=H and R₄ represents hydrogen or a methyl,
or R₃=Me and R₄ represents hydrogen or a methyl,
or R represents C
T-U represents C=N, V represents N, W represents C=O, R₂=H, R₃ does not represent a substituent and R₄=Me,
A represents

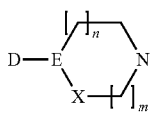

wherein n=m=1, X represents —CH₂— and E represents —CH—, D represents oxygen,
along with the various isomers and mixtures thereof in any proportions, and the pharmaceutically acceptable salts thereof.

According to a further embodiment of the invention, the compounds having general formula I are those wherein:

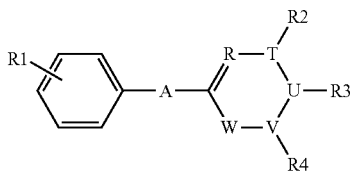

R₁ represents one or a plurality of groups such as: trifluoromethyl, halogen such as F, Cl, Br, methyl, nitro.
R represents nitrogen
T-U represents C=C, V represents N, W represents C=O, R₂ represents Cl or H, R₃=H and R₄=Me,
A represents

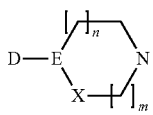

wherein n=m=1, X represents —CH₂— and E represents —CH—, D represents oxygen,
along with the various isomers and mixtures thereof in any proportions, and the pharmaceutically acceptable salts thereof.

The present invention relates to compounds having general formula I characterised in that they are selected from:
1. 6'-Chloro-4'-methyl-4-(2-trifluoromethyl-benzoyl)-3,4,5,6-tetrahydro-2H,4'H-[1,2']bipyrazinyl-3'-one
2. 4'-Methyl-4-(2-trifluoromethyl-benzoyl)-3,4,5,6-tetrahydro-2H,4'H-[1,2']bipyrazinyl-3'-one
3. (4-[1,2,4]Triazin-3-yl-piperazin-1-yl)-(2-trifluoromethyl-phenyl)-methanone
4. (5-Fluoro-2-trifluoromethyl-phenyl)-(4-[1,2,4]triazin-3-yl-piperazin-1-yl)-methanone
5. 3-[4-(2-Trifluoromethyl-benzyl)-piperazin-1-yl]-[1,2,4]triazine
6. 5-Chloro-3-[4-(2-chloro-phenoxy)-piperidin-1-yl]-1-methyl-1H-pyrazin-2-one
7. 5-Chloro-1-methyl-3-[4-(2-trifluoromethyl-phenoxy)-piperidin-1-yl]-1H-pyrazin-2-one
8. 5-Chloro-3-[4-(2-chloro-5-trifluoromethyl-phenoxy)-piperidin-1-yl]-1-methyl-1H-pyrazin-2-one
9. 5-Chloro-1-methyl-3-(4-o-tolyloxy-piperidin-1-yl)-1H-pyrazin-2-one
10. 1-Methyl-3-(4-o-tolyloxy-piperidin-1-yl)-1H-pyrazin-2-one
11. 1-Methyl-3-[4-(2-trifluoromethyl-phenoxy)-piperidin-1-yl]-1H-pyrazin-2-one
12. 5-Chloro-3-[4-(2-chloro-5-fluoro-phenoxy)-piperidin-1-yl]-1-methyl-1H-pyrazin-2-one
13. 3-[4-(2-Chloro-phenoxy)-piperidin-1-yl]-[1,2,4]triazine
14. 3-[4-(2-Trifluoromethyl-phenoxy)-piperidin-1-yl]-[1,2,4]triazine
15. 3-[4-(2-Chloro-5-fluoro-phenoxy)-piperidin-1-yl]-5-phenyl-[1,2,4]triazine
16. 5-Phenyl-3-[4-(2-trifluoromethyl-phenoxy)-piperidin-1-yl]-[1,2,4]triazine
17. 3-[4-(2-Chloro-5-trifluoromethyl-phenoxy)-piperidin-1-yl]-[1,2,4]triazine
18. 3-[4-(2-Chloro-5-fluoro-phenoxy)-piperidin-1-yl]-[1,2,4]triazine
19. 3-[4-(2-Chloro-5-trifluoromethyl-phenoxy)-piperidin-1-yl]-5,6-dimethyl-[1,2,4]triazine
20. 3-[4-(2-Chloro-5-trifluoromethyl-phenoxy)-piperidin-1-yl]-5,6-diphenyl-[1,2,4]triazine
21. 3-[4-(2-Chloro-5-trifluoromethyl-phenoxy)-piperidin-1-yl]-5,6,7,8-tetrahydro-benzo[1,2,4]triazine
22. 3-[4-(2-Chloro-5-trifluoromethyl-phenoxy)-piperidin-1-yl]-6-methyl-5-(3-trifluoromethyl-phenyl)-[1,2,4]triazine
23. 3-[4-(2-Chloro-5-trifluoromethyl-phenoxy)-piperidin-1-yl]-5,6-di-furan-2-yl-[1,2,4]triazine
24. 3-[4-(2-Chloro-5-trifluoromethyl-phenoxy)-piperidin-1-yl]-5,6-di-pyridin-2-yl-[1,2,4]triazine
25. 3-[4-(2-Chloro-5-fluoro-phenoxy)-piperidin-1-yl]-5-methyl-[1,2,4]triazine
26. 5-Methyl-3-(4-o-tolyloxy-piperidin-1-yl)-[1,2,4]triazine
27. 3-[4-(2-Chloro-5-trifluoromethyl-phenoxy)-piperidin-1-yl]-5-methyl-[1,2,4]triazine
28. 3-[4-(2-Chloro-phenoxy)-piperidin-1-yl]-5-methyl-[1,2,4]triazine
29. 3-(4-o-Tolyloxy-piperidin-1-yl)-[1,2,4]triazine
30. 3-[4-(2-Chloro-5-fluoro-phenoxy)-piperidin-1-yl]-6-methyl-[1,2,4]triazine
31. 6-Methyl-3-(4-o-tolyloxy-piperidin-1-yl)-[1,2,4]triazine
32. 3-[4-(2-Chloro-5-nitro-phenoxy)-piperidin-1-yl]-[1,2,4]triazine
33. 3-[4-(2-Bromo-4,5-difluoro-phenoxy)-piperidin-1-yl]-[1,2,4]triazine
34. 3-[4-(3-Fluoro-5-trifluoromethyl-phenoxy)-piperidin-1-yl]-[1,2,4]triazine
35. 3-[4-(2-Nitro-phenoxy)-piperidin-1-yl]-[1,2,4]triazine 36. 1-[1,2,4]Triazin-3-yl-piperidin-4-yl)-(2-trifluoromethyl-phenyl)-amine
37. 3-[4-(2-Chloro-5-trifluoromethyl-phenoxy)-3-methyl-piperidin-1-yl]-[1,2,4]triazine
38. 3-[4-(2,5-Dichloro-phenoxy)-3-methyl-piperidin-1-yl]-[1,2,4]triazine
39. 5-[4-(2-Chloro-5-trifluoromethyl-phenoxy)-piperidin-1-yl]-2-methyl-2H-pyridazin-3-one
40. 4-[4-(2-Chloro-5-trifluoromethyl-phenoxy)-piperidin-1-yl]-2-methyl-2H-pyridazin-3-one
41. 3-[3-(2-Chloro-5-trifluoromethyl-phenoxymethyl)-azetidin-1-yl]-[1,2,4]triazine
42. 3-[3-(2-Chloro-5-trifluoromethyl-phenoxy)-pyrrolidin-1-yl]-[1,2,4]triazine
43. [(Trans)-2-(2-Chloro-5-trifluoromethyl-phenoxymethyl)-cyclopropyl]-[1,2,4]triazin-3-yl-amine.

The present invention also applies to the various isomers of the compounds having general formula I, particularly including enantiomers, along with the mixtures thereof in any proportions.

The mixtures of the isomers in any proportions also include the racemic mixtures in the case of enantiomers.

The subject matter of the invention also relates the pharmaceutically acceptable salts of the compounds having general formula I.

The present invention also applies to the processes for the chemical preparation of the compounds having general formula I.

The present invention also relates to compounds having general formula I along with the various isomers and mixtures thereof in any proportions, and the pharmaceutically acceptable salts thereof for the use thereof as an SCD-1 enzyme inhibitor.

The present invention also relates to compounds having general formula I along with the various isomers and mixtures thereof in any proportions, and the pharmaceutically acceptable salts thereof for the use thereof as a medicinal product.

The present invention also relates to compounds having general formula I along with the various isomers and mixtures thereof in any proportions, and the pharmaceutically acceptable salts thereof for the use thereof as a cosmetic active ingredient.

The present invention also relates to compounds having general formula I along with the various isomers and mixtures thereof in any proportions, and the pharmaceutically acceptable salts thereof for the use thereof as a medicinal product for treating and/or preventing diseases requiring SCD-1 enzyme activity inhibitors.

The present invention also relates to compounds having general formula I along with the various isomers and mixtures thereof in any proportions, and the pharmaceutically acceptable salts thereof for the use thereof as a medicinal product for treating and/or preventing diseases such as obesity, type 2 diabetes, diabetic dyslipidaemia, hypertriglyceridemia, hypercholesterolaemia, metabolic syndrome, atherosclerosis and the complications thereof, liver steatosis or cardiovascular risks.

The present invention also relates to compounds having general formula I along with the various isomers and mixtures thereof in any proportions, and the pharmaceutically acceptable salts thereof for the use thereof as a medicinal product for treating and/or preventing:
  pathological conditions associated with skin-related lipid disorders and inflammatory and bacterial complications;
  sebum production and/or secretion disorders associated with hyperandrogenism (regardless of the cause—iatrogenic, adrenal, or ovarian)

Dermatological diseases associated with a skin-related lipid disorder are, for example, acne, psoriasis, hirsutism, rosacea, seborrheic dermitis, hyperseborrhoea, or eczema.

The invention also relates to compounds having general formula (I) along with pharmaceutically acceptable bases and acids, and the various isomers, along with the mixtures thereof in any proportions for the use thereof as a medicinal product for treating and/or preventing cancer.

In particular, the term cancer refers to liquid tumours and/or solid tumours, such as melanomas, colorectal cancer, lung, prostate, bladder, breast, uterine, oesophageal, stomach, pancreatic, liver cancer, ovarian cancer, leukaemia particularly lymphomas and myelomas, ENT-related cancer and brain cancer.

The invention also relates to compositions characterised in that they contain, as an active ingredient, a compound having general formula I or any of the isomers thereof and the mixtures thereof in any proportions, or any of the pharmaceutically acceptable salts thereof.

The invention also relates to a pharmaceutical composition characterised in that it contains a compound having general formula I or any of the isomers thereof and the mixtures thereof in any proportions, or any of the pharmaceutically acceptable salts thereof in association with any suitable excipient.

The invention also relates to a pharmaceutical composition characterised in that it contains a compound having general formula I or any of the isomers thereof and the mixtures thereof in any proportions, or any of the cosmetically acceptable salts thereof in association with any suitable excipient.

The pharmaceutical composition according to the invention may be administered in association with an anti-diabetic drug such as biguanides (for example metformin), various forms of insulin, sulphonylureas (for example carbutamide, glibornuride, glipizide, gliclazide, glibenclamide, glimepiride), meglitinides, PPAR modulators (for example pioglitazone), alpha-glucosidase inhibitors (for example acarbose, miglitol, voglibose), DPP-4 inhibitors (for example sitagliptin, vildagliptin), amylin analogues (for example pramlintide), glucagon-like peptide-1 analogues (for example exenatide, liraglutide), SGLT2 inhibitors or 11β-HSD1 inhibitors.

The pharmaceutical composition may be administered in association with an anti-obesity drug such as orlistat or sibutramine.

The pharmaceutical composition may be administered in association with a compound suitable for use for treating or preventing pathological conditions associated with skin-related lipid disorders and inflammatory and bacterial complications or sebum production and/or secretion disorders associated with hyperandrogenism (regardless of the cause=iatrogenic, adrenal, or ovarian), such as retinoids, antibiotics, antibacterials, or antiandrogens.

Retinoids are vitamin A derivatives routinely used for treating dermatological diseases.

The retinoids in question particularly include: retinol, retinal, tretinoin, isotretinoin, alitretinoin, etretinate and the metabolite thereof acitretin, tazarotene, bexarotene or adapalene.

The term antibiotics refers to those, for example targeting *Propionibacterium acnes* bacteria involved in some dermatological diseases such as acne. They may consist of local antibiotics such as clindamycin or erythromycin. They may also consist of oral antibiotics such as doxycycline, minocycline or tetracycline.

The antibacterials are those routinely used for treating some dermatological diseases such as benzoyl peroxide, or azelaic acid.

The anti-androgens suitable for being associated are for example progesterone, oestrogen, finasteride, dutasteride, cyproterone optionally in association with ethinyl oestradiol, flutamide, nilutamide, or bicalutamide.

The pharmaceutical composition may be administered in association with a compound suitable for use in the treatment or prevention of cancer in association with other anticancer treatments, whether they are cytotoxic and/or cytostatic, such as platinum derivatives, taxanes, vincas, 5-FU, to increase therapeutic efficacy for treating refractory tumours to routine treatments.

The pharmaceutical composition according to the invention may be administered by the parenteral route, oral route, rectal route or topical route. Advantageously, the pharmaceutical composition according to the invention is administered by the topical route.

The pharmaceutical compositions for parenteral administration are sterile and may be in the form of aqueous or non-aqueous solutions, suspensions or emulsions.

The pharmaceutical compositions for oral administration may be in solid or liquid form. The solid compositions for oral administration include for example tablets, pills, powders (gelatine capsules, cachets) or granules.

The liquid compositions for oral administration include solutions, suspensions, emulsions and syrups.

The pharmaceutical compositions for rectal administration are, for example, suppositories or rectal capsules.

The pharmaceutical compositions for topical administration may be in the form of liquid products (solutions, suspensions), semi-solid products (cream, gel, ointment, paste, plaster, shampoo, mousse, lotion, serum, mask), or solid products (powder, solid stick) and may optionally be packaged in aerosol or spray form.

SUMMARY

The compounds according to the present invention may be synthesised using the synthesis processes described below or using synthesis methods known to those skilled in the art.

Method 1

The synthesis of the compounds having general formula I is characterised (diagram 1) by the condensation of a derivative having general formula II

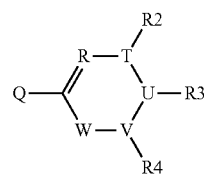

wherein:

Q represents Cl if R represents N, T-U represents C=C, V represents N, W represents C=O, $R_2$, $R_3$ and $R_4$ and, in this case, as described above in general formula I, Or Q represents $CH_3S$ or $CH_3S(O)_2$ if R represents N, T-U represents N=C, V—W represents C=N, $R_2$ does not represent a substituent, and $R_3$ and $R_4$ are, in this case, as described above in general formula I, Or Q represents iodine if R represents C, $TR_2$ represents C=O, U represents N, $R_3$ is, in this case, as described above in general formula I, V—W represents N=CH and $R_4$ does not represent a substituent, Or Q represents $CF_3S(O)_2O$ if R represents C, T-U represents C=N, V represents N, W represents C=O, $R_3$ does not represent a substituent and $R_2$ and $R_4$ are, in this case, as described above in general formula I, with a derivative having general formula III

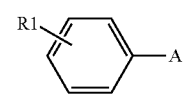

where A and $R_1$, are as described above in general formula I. This reaction may be carried out in the absence of a base in solvents such as tetrahydrofuran or ethanol (in microwaves) or in the presence of a base such as triethylamine in solvents such as n-butanol or acetonitrile;

Diagram 1

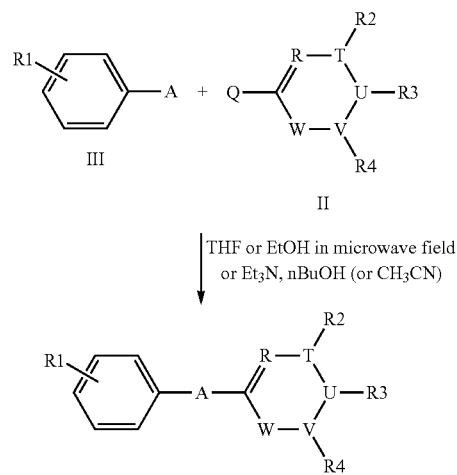

Method 2

This method for the synthesis of compounds having general formula I (diagram 2) is characterised by the condensation of a derivative having general formula IV.

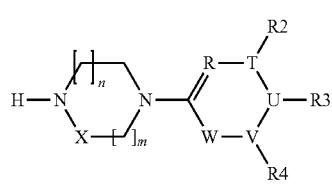

wherein X, n, m, R, T, U, V, W, $R_2$, $R_3$ and $R_4$ represent groups as described above in general formula I with a derivative having general formula V.

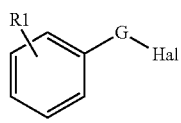

wherein Hal represents a halogen such as Cl or Br, G represents C=O or —CH$_2$— and R$_1$ is as described above in general formula I.

This reaction may be carried out in the presence of a base such as triethylamine or diisopropylethylamine in solvents such as dichloromethane or toluene (particularly if G represents —CH$_2$—):

Diagram 2

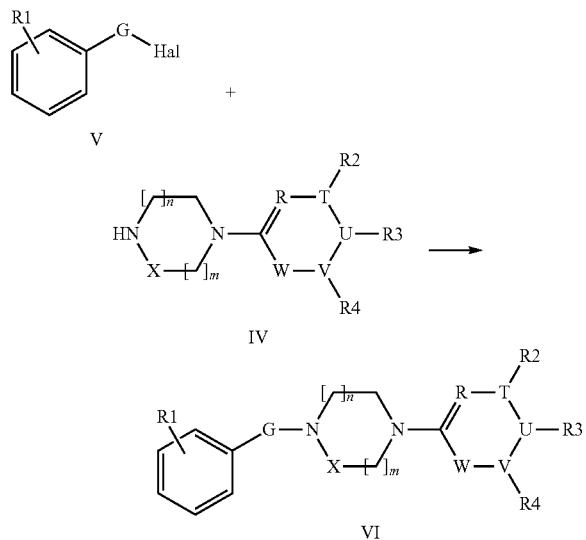

Method 3

This method for the synthesis of compounds having general formula I is characterised (diagram 3) by the condensation of a derivative having general formula VII

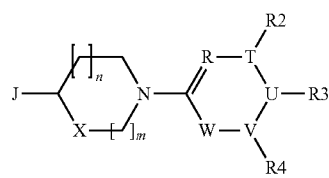

wherein J represents OH or NH$_2$, and X, n, m, R, T, U, V, W, R$_2$, R$_3$ and R$_4$ are as defined above in general formula I with a derivative having general formula VIII:

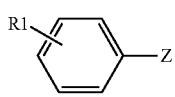

wherein R$_1$ is as defined in general formula I and Z represents OH or Br.

This reaction may be carried out under operating conditions such as those for Mitsunobu coupling in the presence of triphenylphosphine, diisopropylazodicarboxylate in THF (if J and Z represent OH) and under operating conditions such as those for Buchwald coupling in the presence of bis(diphenylphosphino)-1,1'-binaphthyl, dipalladium bis[dibenzylideneacetone], sodium tert-butoxide in toluene (if J=NH$_2$ and Z=Br).

Diagram 3

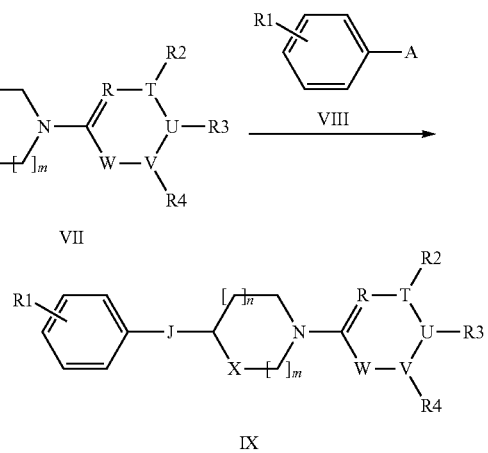

Method 4

This method for the synthesis of the compounds having general formula I is characterised (diagram 4) by the dehalogenation of position 6 of the compounds having formula X wherein R$_2$ represents Br or Cl, R and V represent a nitrogen, T-U represents C=O, W represents C=O, R$_1$ represents trifluoromethyl, a halogen such as F, Cl, a C$_1$-C$_4$ linear or branched alkyl, trifluoromethoxy, acetyl, and R$_3$, R$_4$, D, E, X, n, m, are as described above in general formula I.

Diagram 4

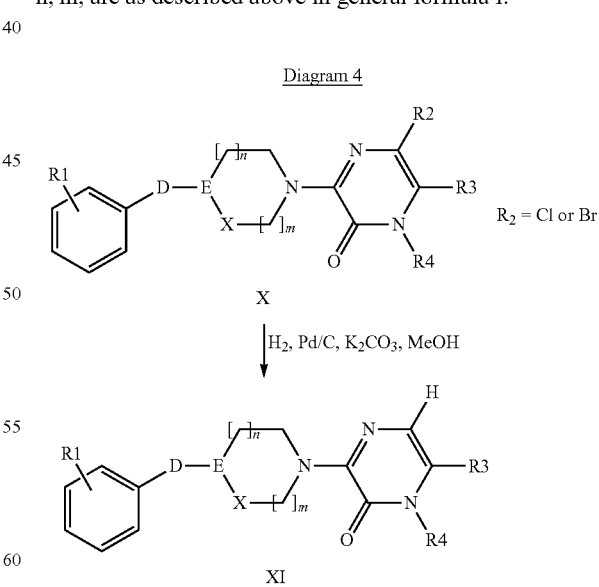

The operating conditions are as for hydrogen pressure in the presence of carbon-activated palladium and potassium carbonate in methanol.

The intermediate and final compound may be, if required, purified according to one or a plurality of purification methods selected from extraction, filtration, silica gel chromatography, normal or reverse-phase preparative HPLC, crystallisation.

The raw materials used in the processes described above are commercial or readily accessible to those skilled in the art according to the processes described in the literature.

The following examples illustrate the invention without limiting the scope thereof.

The elemental analyses and the mass and NMR spectra confirm the structures of the compounds.

INTERMEDIATES

Intermediates 1 a) 4-(2-trifluoromethyl-phenoxy)-piperidine hydrochloride (1a)

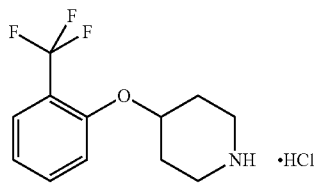 [SMILES: FC(F)(F)c1ccccc1OC1CCNCC1 ; Cl]

21.6 g (107 mmoles) of BOC-4-hydroxy-piperidine is placed in the presence of 19.1 g (118 mmoles) of 2-trifluoromethylphenol, 33.8 g (128 mmoles) of triphenylphosphine in 300 ml of THF. At 0° C., 24.3 ml (128 mmoles) of DEAD is added drop by drop. The reaction medium is stirred for one hour at ambient temperature and heated for 24 hours at 70° C. After concentration, the residue obtained is taken up with ether, washed with a sodium hydroxide solution (1N) and with a saturated NaCl solution. After drying on $Na_2SO_4$, the organic phases are concentrated to dryness, and taken up with a petroleum ether-$Et_2O$ mixture: 70-30 to remove the triphenylphosphine oxide. After filtration, the filtrate is concentrated, the residue obtained is purified by silica flash chromatography (petroleum ether-AcOEt, 100-0 to 80-20 gradient for 50 min). 17.8 g of clear oil is obtained (48% yield). TLC silica gel 60 F 254 Merck, Petroleum ether-AcOEt: 90-10, Rf=0.26. This oil is placed in 300 ml of dichloromethane in the presence of 23 ml (309 mmoles) of TFA, and this solution is stirred for 24 hours at ambient temperature. The medium is concentrated, the residue obtained is taken up with AcOEt, washed with an aqueous sodium hydroxide solution (1N), and with NaCl-saturated water. After drying on $Na_2SO_4$, the organic phases are concentrated to dryness. 11.9 g of clear oil is obtained (94% yield). This oil is solubilised in the minimum EtOH and treated with 9 ml of an HCl solution (5N in iPrOH). After stirring at ambient temperature for 3 hours, the precipitate is filtered, rinsed with ethyl ether and dried. 9.6 g of intermediate 1a is thus obtained in white solid form (70% yield). TLC silica gel 60 F 254 Merck, $CH_2Cl_2$-MeOH-$NH_4OH$: 90-9-1, Rf=0.26.

b) Intermediates 1b-1d

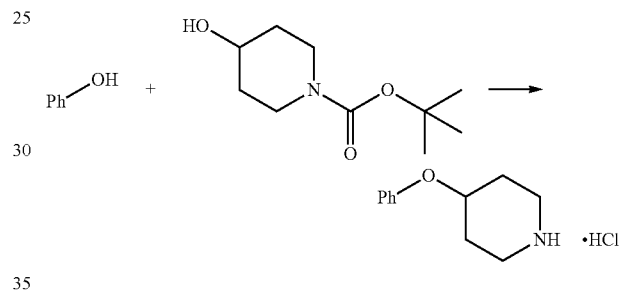

Intermediates 1b-1d are synthesised according to the procedure described for the synthesis of 1a using various Ph-OH phenols.

TABLE 1

| | Intermediates 1b-1d | | | | |
|---|---|---|---|---|---|
| PhOH | | Total yield | TLC | State | Intermediates 1b-1d |
| Cl-C6H3(OH)-CF3 | | 79% | $CH_2Cl_2$—MeOH—$NH_4OH$: 95-4.5-0.5 Rf = 0.37 | solid | 1b: 4-(2-chloro-5-trifluoromethyl-phenoxy)-piperidine hydrochloride |
| Cl-C6H3(OH)-F | | 70% | $CH_2Cl_2$—MeOH—$NH_4OH$: 90-9-1 Rf = 0.24 | solid | 1c: 4-(2-chloro-5-fluoro-phenoxy)-piperidine hydrochloride |

TABLE 1-continued

Intermediates 1b-1d

| PhOH | Total yield | TLC | State | Intermediates 1b-1d |
|---|---|---|---|---|
| 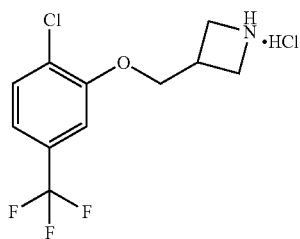 [SMILES: FC(F)(F)c1ccc(Cl)c(OCC2CNC2)c1 ; Cl] | 44% | CH$_2$Cl$_2$—MeOH—NH$_4$OH: 90-9-1 Rf = 0.26 | solid | 1d: 4-(2-chloro-phenoxy)-piperidine hydrochloride |

TLC: silica gel 60 F 254 Merck.

c) 3-(2-chloro-5-trifluoromethyl-phenoxymethyl)-azetidine hydrochloride (1e)

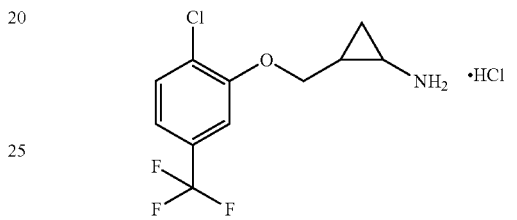

3 g (11.84 mmoles) of diphenylmethyl-3-(hydroxymethyl) azetidine is placed in the presence of 2.55 g (13.02 mmoles) of 2-chloro-5-(trifluoromethyl)phenol and 3.72 g (14.20 mmoles) of triphenylphosphine in 70 ml of THF. At 0° C., 2.23 ml (14.20 mmoles) of DEAD is added drop by drop. The reaction medium is stirred for one hour at ambient temperature and heated for 24 hours at 70° C. After concentration, the residue obtained is taken up with CH$_2$Cl$_2$ and washed with a sodium hydroxide solution (1N). After drying on MgSO$_4$, the organic phases are concentrated to dryness and the residue obtained is purified by silica flash chromatography (petroleum ether-AcOEt, 100-0 to 85-15 gradient for 50 min). 5 g of yellow oil is obtained (97% yield). TLC silica gel 60 F 254 Merck, Petroleum ether-AcOEt: 80-20, Rf=0.39. This oil is placed in 75 ml of 1,2-dichloroethane in the presence of 3.71 ml (34.44 mmoles) of 1-chloroethylchloroformate and this solution is stirred for 20 hours at 70° C. 75 ml of MeOH is then added and the reaction medium is stirred for 24 hours at 70° C. After concentration to dryness, the residue obtained is triturated in petroleum ether, filtered and rinses with petroleum ether. The solid obtained is taken up with water and treated with NaHCO$_3$ and extracted with CH$_2$Cl$_2$. After drying on MgSO$_4$, the organic phases are concentrated to dryness and the residue obtained is purified by silica flash chromatography (CH$_2$Cl$_2$-MeOH-NH$_4$OH, 100-0-0 to 90-9-1 gradient for 50 min). 0.69 g of beige solid is obtained. This solid is solubilised in the minimum EtOH and treated with 0.52 ml of an HCl solution (5N in iPrOH). After stirring at ambient temperature for 3 hours, the precipitate is filtered, rinses with ethyl ether and dried. 0.691 g of intermediate 1e is thus obtained in white solid form (20% yield). TLC silica gel 60 F 254 Merck, CH$_2$Cl$_2$-MeOH-NH$_4$OH: 90-9-1, Rf=0.15.

d) trans 2-(2-chloro-5-trifluoromethyl-phenoxymethyl)-cyclopropylamine hydrochloride (1f)

The intermediate 1f is synthesised according to the procedure described for the synthesis of 1a from 2-chloro-5-(trifluoromethyl)phenol and trans-(2-hydroxymethyl-cyclopropyl)-carbamic acid tert-butyl ester and, the amine function deprotection step is carried out in an HCl solution (4N in dioxane). 1f is isolated in solid form with a 95% yield.

TLC silica gel 60 F 254 Merck, CH$_2$Cl$_2$-MeOH-NH$_4$OH: 90-9-1, Rf=0.2.

e) 4-o-Tolyloxy-piperidine (1g)

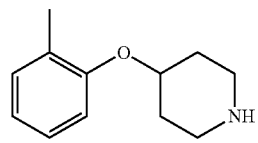

9 g (44.7 mmoles) of BOC-4-hydroxy-piperidine are placed in 30 ml of dichloromethane at 0° C. 3.5 ml (44.7 mmoles) of mesyl chloride and 8 ml (58.1 mmoles) of triethylamine is added slowly. The reaction medium is stirred for 3 hours at 0° C., and filtered on a frit. The filtrate is washed with water. After drying on MgSO$_4$, the organic phase is concentrated to dryness. 12.48 g of oil is obtained (quantitative yield). TLC silica gel 60 F 254 Merck, CH$_2$Cl$_2$-MeOH: 95-5, Rf=0.60. 1.81 g (6.47 mmoles) of this oil is placed in the presence of 0.67 ml (6.47 mmoles) of 2-methylphenol and 4.09 g (12.5 mmoles) of cesium carbonate in 10 ml of DMF. This solution is stirred for 24 hours at 70° C. After concentrating the reaction medium, the residue obtained is purified by flash chromatography (petroleum ether-AcOEt, 100-0 to 85-15 gradient over 60 min). 0.9 g of clear oil is obtained (yield: 48%). TLC silica gel 60 F 254 Merck, Petroleum ether-AcOEt: 95-5, Rf=0.28. This oil is placed in 5 ml of CH$_2$Cl$_2$ in the presence of 0.58 ml (7.81 mmoles) of TFA. The solution is stirred for 6 hours at ambient temperature. After concentrating the reaction medium, the residue is taken up with AcOEt, washed with a sodium hydroxide solution (1N), and with NaCl-saturated water. After drying on MgSO₄, the organic phase is concentrated to dryness and 0.46 g of intermediate 1g in light oil form is obtained (62% yield).

TLC silica gel 60 F 254 Merck, CH₂Cl₂-MeOH: 95-5, Rf=0.17.

f) (2-trifluoromethyl-phenyl)-piperazin-1-yl-methanone hydrochloride (1h)

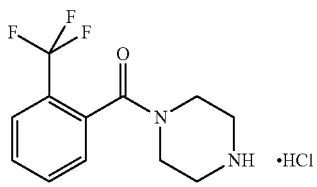 [SMILES: O=C(c1ccccc1C(F)(F)F)N1CCNCC1 ; Cl]

16.20 g (86.90 mmoles) of BOC-piperazine is placed in 120 ml of CH₂Cl₂ and 23 ml (165 mmoles) of Et₃N in nitrogen. At 0° C., 17.27 g (82.80 mmoles) of (2-trifluoromethyl)-benzoyl chloride is added drop by drop and the reaction medium is stirred for 30 min at 0° C. and for 2 hours at ambient temperature. After concentration to dryness, the residue obtained is taken up with water and extracted with AcOEt. After drying on Na₂SO₄, the organic phases are concentrated to dryness and the residue obtained is triturated in petroleum ether and filtered, rinsed and vacuum-dried. 28.5 g of beige solid is obtained (96% yield). TLC silica gel 60 F 254 Merck, hexane-AcOEt: 50-50, Rf=0.24. This solid is placed in the presence of 100 ml of an HCl solution (5N in iPrOH) in 60 ml of EtOH and the reaction medium is stirred for 2 hours at 65° C. After concentration to dryness, the residue obtained is triturated in 200 ml of diethyl ether and filtered, rinsed and vacuum-dried. 22.6 g of intermediate 1h is thus obtained in white solid form (96% yield). TLC silica gel 60 F 254 Merck, CH₂Cl₂-MeOH-NH₄OH: 90-9-1, Rf=0.34.

Intermediates 2 a) 3-Methylsulphanyl-[1,2,4]triazine (2a)

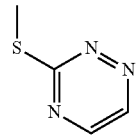

20 g (219 mmoles) of thiosemicarbazide is placed in 100 ml of ethanol. At 0° C., 13.8 ml (219 mmoles) of iodomethane is added drop to drop. The mixture is heated for 4 hours at 80° C. After cooling, the precipitate formed is filtered, and washed with petroleum ether. 48.63 g of yellow powder is obtained (yield: 95%). TLC silica gel 60 F 254 Merck, CH₂Cl₂-AcOEt: 90-10, Rf=0.18. 15 g (64.35 mmoles) of this solid is placed in 100 ml of chilled water. A solution of 50 g (64.35 mmoles) of sodium hydrogen carbonate in 50 ml of water is added. At 0° C., 9.3 ml (64.35 mmoles) of glyoxal is added drop by drop. The reaction medium is stirred for 18 hours at ambient temperature. After extracting the reaction medium with dichloromethane, the organic phases are dried on MgSO₄, and concentrated to dryness. 7.23 g of intermediate 2a is obtained in yellow oil form (yield: 88%).

TLC silica gel 60 F 254 Merck, CH₂Cl₂-AcOEt: 95-5, Rf=0.4.

b) Intermediates 2b-21

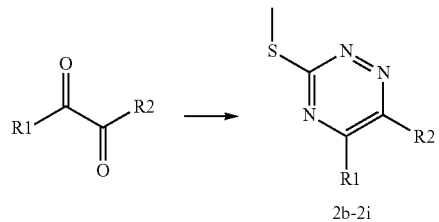

Intermediates 2b-21 are synthesised according to the procedure described for the synthesis of 2a using various glyoxal derivatives in water at ambient temperature or in refluxing ethanol.

TABLE 2

| intermediates 2b-2i | | | | |
|---|---|---|---|---|
| R1(C=O)₂R2 | Yield | TLC | State | intermediates 2b-2i |
| (phenyl glyoxal, PhC(O)CHO) | 92% | CH₂Cl₂—MeOH: 95-5 Rf = 0.55 | solid | 2b: 3-Methylsulphanyl-5-phenyl-[1,2,4]triazine |
| (methylglyoxal, CH₃C(O)CHO) | 60% | CH₂Cl₂—AcOEt: 95-5 Rf = 0.41 | solid | 2c: 5-Methyl-3-methylsulphanyl-[1,2,4]triazine |

TABLE 2-continued intermediates 2b-2i

| R1(C=O)2R2 | Yield | TLC | State | intermediates 2b-2i |
|---|---|---|---|---|
| | 100% | $CH_2Cl_2$—MeOH: 95-5<br>Rf = 0.64 | solid | 2d: 5,6-Dimethyl-3-methylsulphanyl-[1,2,4]triazine |
| | 100% | $CH_2Cl_2$—AcOEt: 95-5<br>Rf = 0.59 | solid | 2e: 3-Methylsulphanyl-5,6-diphenyl-[1,2,4]triazine |
| | 95% | $CH_2Cl_2$—AcOEt: 80-20<br>Rf = 0.59 | solid | 2f: 3-Methylsulphanyl-5,6,7,8-tetrahydro-benzo[1,2,4]triazine |
| | 39% | $CH_2Cl_2$—AcOEt: 90-10<br>Rf = 0.68 | solid | 2g: 6-Methyl-3-methylsulphanyl-5-(3-trifluoromethyl-phenyl)-[1,2,4]-triazine |
| | 100% | $CH_2Cl_2$—AcOEt: 95-5<br>Rf = 0.68 | solid | 2h: 5,6-Di-furan-3-yl-3-methylsulphanyl-[1,2,4]triazine |
| | 92% | $CH_2Cl_2$—MeOH: 95-5<br>Rf = 0.67 | solid | 2i: 3-Methylsulphanyl-5,6-di-pyridin-2-yl-[1,2,4]triazine |

TLC: silica gel 60 F 254 Merck.

c) 6-Methyl-3-methylsulphanyl-[1,2,4]triazine (2j)

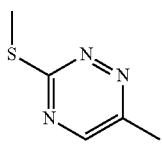

20 g (219 mmoles) of thiosemicarbazide is placed in 100 ml of ethanol. At 0° C., 13.8 ml (219 mmoles) of iodomethane is added drop by drop. The mixture is heated for 4 hours at 80° C. After cooling, the medium is filtered, the precipitate formed is washed with petroleum ether. 48.63 g of yellow powder is obtained (yield: 95%). TLC silica gel 60 F 254 Merck, $CH_2Cl_2$-AcOEt: 90-10, Rf=0.18. 4 g (17.16 mmoles) of this solid is placed in 25 ml of methanol. 2.05 ml (17.16 mmoles) pyruvic aldehyde-dimethylacetal are added drop by drop. The reaction medium is heated for 4 hours at 70° C. After concentration, the residue obtained is taken up with a saturated NaCl solution and extracted with ethyl acetate. After drying on $MgSO_4$, the organic phases are concentrated to dryness. The residue obtained is purified by flash chromatography ($CH_2Cl_2$-AcOEt gradient: 100-0 to 90-10). 1.11 g of intermediate 2j is obtained in yellow solid form (yield: 46%).

TLC silica gel 60 F 254 Merck, $CH_2Cl_2$-AcOEt: 90-10, Rf=0.34.

Intermediates 3 a) 3-Methanesulphonyl-5,6-dimethyl-[1,2,4]triazine (3a)

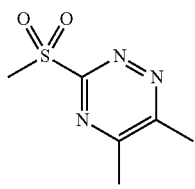

3.57 g (23 mmoles) of intermediate 2d is placed in 90 ml of dichloromethane. At 0° C., 11.3 g (46 mmoles) of meta-chloroperbenzoic acid is added in portions. The mixture is stirred at ambient temperature for 2 hours. After filtering the precipitate, the filtrate is concentrated, the residue is purified by flash chromatography (Petroleum ether 100 for 6 min, and CH$_2$Cl$_2$-AcOEt gradient: 100-0 to 20-80 for 40 min). 3.6 g of intermediate 3a is obtained in yellow solid form (yield: 83%).

TLC silica gel 60 F 254 Merck, CH$_2$Cl$_2$-AcOEt: 90-10, Rf=0.31.

b) Intermediates 3b-3g

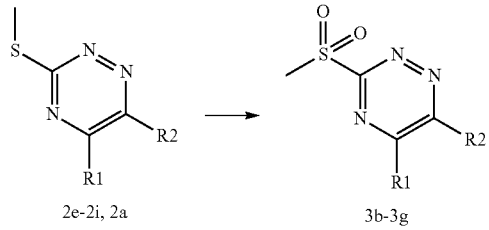

Intermediates 3b-3g are synthesised from compounds 2e-2i, 2a according to the procedure described for the synthesis of 3a.

TABLE 3 intermediates 3b-3g

| Initial synthons | Yield | TLC | State | intermediates 3b-3g |
|---|---|---|---|---|
| 2e | 75% | CH$_2$Cl$_2$—AcOEt: 90-10 Rf = 0.56 | solid | 3b: 3-Methanesulphonyl-5,6-diphenyl-[1,2,4]triazine |
| 2f | 43% | CH$_2$Cl$_2$—AcOEt: 80-20 Rf = 0.42 | solid | 3c: 3-Methanesulphonyl-5,6,7,8-tetrahydro-benzo[1,2,4]triazine |
| 2g | 94% | CH$_2$Cl$_2$—AcOEt: 90-10 Rf = 0.68 | solid | 3d: 3-Methanesulphonyl-6-methyl-5-(3-trifluoromethyl-phenyl)-[1,2,4]triazine |
| 2h | 53% | CH$_2$Cl$_2$—AcOEt: 75-25 Rf = 0.80 | solid | 3e: 5,6-Di-furan-2-yl-3-methanesulphonyl-[1,2,4]triazine |
| 2i | 35% | CH$_2$Cl$_2$—MeOH: 95-5 Rf = 0.37 | solid | 3f: 3-Methanesulphonyl-5,6-di-pyridin-2-yl-[1,2,4]triazine |
| 2a | 18% | CH$_2$Cl$_2$—AcOEt: 95-5 Rf = 0.23 | solid | 3g: 3-Methanesulphonyl-[1,2,4]triazine |

Intermediates 4 a) 5-Iodo-2-methyl-2H-pyridazin-3-one (4a)

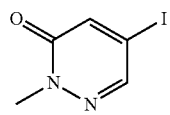

1.55 g (8.65 mmoles) of 4,5-dichloro-2-methyl-2H-pyridazin-3-one is placed in 50 ml of an aqueous 57% iodidric acid solution. The mixture is heated for 24 hours at 137° C. After returning to ambient temperature, the reaction medium is poured onto an aqueous sodium thiosulphate solution (20 g in 250 ml of water). The mixture is taken up with dichloromethane, washed with water, and with a saturated NaCl solution. After drying on Na$_2$SO$_4$, the organic phase is concentrated to dryness. The residue obtained is triturated in a 50:50 dichloromethane-methanol mixture, the precipitate is isolated by filtration. 3.45 g of intermediate 4a is obtained in yellow powder form (yield: quantitative).

TLC silica gel 60 F 254 Merck, CH$_2$Cl$_2$-AcOEt: 70-30, Rf=0.4.

b) Trifluoro-methanesulphonic acid 2-methyl-3-oxo-2,3-dihydro-pyridazin-4-yl ester (4b)

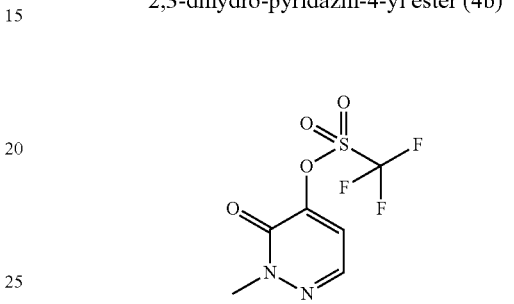

3.13 g (27.93 mmoles) of potassium tertbutylate is placed in 25 ml of tetrahydrofuran. At 0° C., a solution of 1.16 ml (27.93 mmoles) of methanol in 10 ml of tetrahydrofuran is added. The mixture is stirred at 0° C. for 10 min. This solution is added drop by drop to mixture cooled to 0° C. of 5 g (27.93 mmoles) of 4,5-dichloro-2-methyl-2H-pyridazin-3-one solubilised in 40 ml of tetrahydrofuran, the temperature of the medium remains below 3° C. during the addition. The mixture is stirred for 1 hour at 0° C., and for 3 hours at ambient temperature. The medium is taken up with dichloromethane and washed with water. After drying on Na$_2$SO$_4$, the organic phase is concentrated to dryness. The residue obtained is purified by flash chromatography (CH$_2$Cl$_2$-AcOEt: 95-5). 4.45 g of white solid is obtained (yield: 91%). TLC silica gel 60 F 254 Merck, CH$_2$Cl$_2$-AcOEt: 90-10, Rf=0.55. 3.37 g (19.3 mmoles) of this solid is placed in 150 ml of tetrahydrofuran in the presence of 2.7 ml (19.3 mmoles) of triethylamine and 0.67 g of 10% palladium on carbon. The medium is placed under hydrogen pressure (7 bar) and left under stirring for 48 hours. After filtering the reaction medium on celite, the filtrate is concentrated. The residue obtained is purified by flash chromatography (CH$_2$Cl$_2$-AcOEt gradient: 90-10 to 10-90). 2.35 g of white solid is obtained (yield: 86%). TLC silica gel 60 F 254 Merck, CH$_2$Cl$_2$-AcOEt: 50-50, Rf=0.17. 2.35 g (16.7 mmoles) of this solid is placed in 250 ml of water in the presence of 9.6 g (16.7 mmoles) of potassium hydroxide. The mixture is heated to 100° C. for 24 hours. The medium cooled to 0° C. is brought to pH 1-2 by adding an aqueous concentrated hydrochloric acid solution. After concentration to dryness, the residue is taken up with a dichloromethane/methanol mixture, the minerals are removed by filtration and the filtrate is concentrated to dryness. The residue obtained is purified by flash chromatography (CH$_2$Cl$_2$-MeOH: 95-5). 1.94 g of pink solid is obtained (yield: 92%). TLC silica gel 60 F 254 Merck, CH$_2$Cl$_2$-MeOH: 80-20, Rf=0.49. 1 g (7.92 mmoles) of this solid is placed in nitrogen in 15 ml of dichloromethane. At −9° C., 1.45 ml (10.3 mmoles) of triethylamine is added, followed by 1.8 ml (10.7 mmoles) of trifluoromethanesulphonic anhydride. After stirring for 20 min to −7° C., 5 ml of an aqueous 1N hydrochloric acid solution is added. The organic phase is washed with water, and with an aqueous 1% sodium bicarbonate solution, followed by a saturated NaCl solution. After drying on Na$_2$SO$_4$, the organic phases are concentrated to dryness. 1.9 g of intermediate 4b is obtained in pink solid form (yield: 93%).

TLC silica gel 60 F 254 Merck, CH$_2$Cl$_2$-MeOH: 95-5, Rf=0.78.

d) 3,5-Dichloro-1-methyl-1H-pyrazin-2-one (4c)

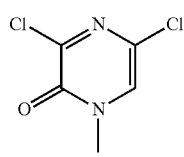

3.29 g (30.8 mmoles) of methylamino-acetonitrile hydrochloride is placed in the presence of 19.6 g (154 mmoles) of oxalyl chloride in 30 ml of 1,2-dichlorobenzene. The mixture is heated for 8 hours at 80° C. After concentrating the reaction medium to dryness, the residue obtained is purified by flash chromatography (Petroleum ether-CH$_2$Cl$_2$ gradient 100-0 to 0-100). 3.35 g of intermediate 4c is obtained in beige powder form (yield: 60%).

TLC silica gel 60 F 254 Merck, CH$_2$Cl$_2$-MeOH: 90-10, Rf=0.79.

Intermediates 5 a) 3-piperazin-1-yl-[1,2,4]triazine (5a)

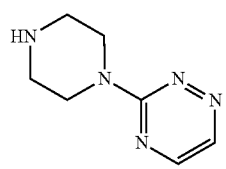 [SMILES: c1cnc(N2CCNCC2)nn1]

3.45 g (40.1 mmoles) of piperazine is placed in the presence of 1.7 g (13.4 mmoles) of intermediate 2a in 1-butanol. 6.5 ml (47 mmoles) of triethylamine is added and the mixture is heated for 24 hours at 120° C. After concentrating the reaction medium, the residue obtained is taken up with ethyl acetate and washed with water. After drying on MgSC$_4$, the organic phase is concentrated to dryness. The residue obtained is purified by flash chromatography (CH$_2$Cl$_2$-MeOH-NH$_4$OH gradient: 100-0-0 to 90-9-1). 1.52 g of intermediate 5a is obtained in brown oil form (yield: 69%).

TLC silica gel 60 F 254 Merck, CH$_2$Cl$_2$-MeOH-NH$_4$OH: 90-9-1, Rf=0.26.

b) 1-[1,2,4]Triazin-3-yl-piperidin-4-ylamine (5b)

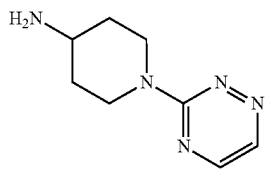 [SMILES: NC1CCN(c2nccnn2)CC1]

Intermediate 5b is synthesised from piperidin-4-ylamine and the precursor 2a according to the procedure described for the synthesis of 5a. Intermediate 5b is isolated in solid form with a 71% yield.

TLC silica gel 60 F 254 Merck, CH$_2$Cl$_2$-MeOH: 95-5, Rf=0.1.

c) 3-Methyl-1-[1,2,4]triazin-3-yl-piperidin-4-ol (5c)

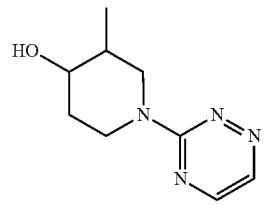

Intermediate 5c is synthesised from 3-methyl-piperidin-4-ol and the precursor 2a according to the procedure described for the synthesis of 5a. Intermediate 5c is isolated in solid form with a 47% yield.

TLC silica gel 60 F 254 Merck, CH$_2$Cl$_2$-MeOH: 95-5, Rf=0.4.

d) 1-[1,2,4]Triazin-3-yl-pyrrolidin-3-ol (5d)

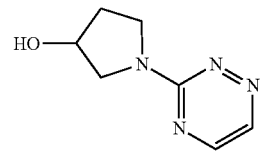 [SMILES: OC1CCN(c2nccnn2)C1]

Intermediate 5d is synthesised from pyrrolidin-3-ol and the precursor 2a according to the procedure described for the synthesis of 5a. Intermediate 5d is isolated in oil form with a 92% yield.

TLC silica gel 60 F 254 Merck, CH$_2$Cl$_2$-MeOH: 95-5, Rf=0.5.

27
e) Intermediates 5e-5g

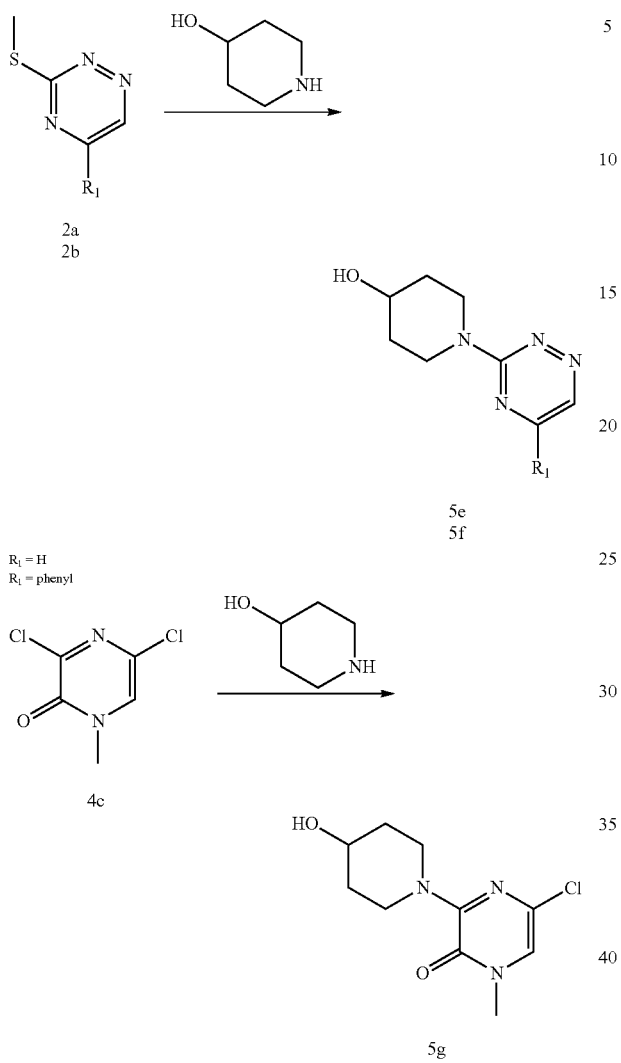

R₁ = H
R₁ = phenyl

Intermediates 5e-5g are synthesised from compounds 2a, 2b and 4c and piperidin-4-ol respectively according to the procedure described for the synthesis of 5a.

TABLE 4

| | | | intermediates 5e-5g | | |
|---|---|---|---|---|---|
| Initial synthons | Yield | TLC | | State | intermediates 5e-5g |
| 2a | 63% | CH₂Cl₂—MeOH—NH₄OH: 90-9-1 Rf = 0.43 | | solid | 5e: 1-[1,2,4]Triazin-3-yl-piperidin-4-ol |
| 2b | 84% | CH₂Cl₂—MeOH: 95-5 Rf = 0.26 | | solid | 5f: 1-(5-Phenyl-[1,2,4]triazin-3-yl)-piperidin-4-ol |
| 4c | 60% | CH₂Cl₂—MeOH: 95-5 Rf = 0.28 | | solid | 5g: 5-Chloro-3-(4-hydroxy-piperidin-1-yl)-1-methyl-1H-pyrazin-2-one |

TLC silica gel 60 F 254 Merck

28
EXAMPLES

Example 1

6'-Chloro-4'-methyl-4-(2-trifluoromethyl-benzoyl)-3,4,5,6-tetrahydro-2H,4'H-[1,2']bipyrazinyl-3'-one (1)

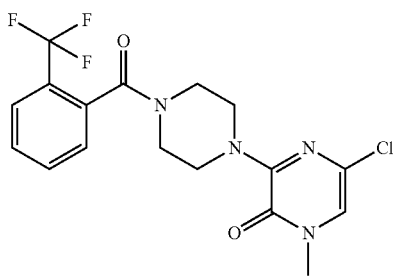 [SMILES: Cn1cc(Cl)nc(N2CCN(C(=O)c3ccccc3C(F)(F)F)CC2)c1=O]

Compound 1 is prepared according to synthesis method 1: 1.76 g (5.97 mmoles) of derivative 1 h and 1.13 g (6.31 mmoles) of pyrazinone 4c are placed in 3 ml of butanol-1 in the presence of 4 ml (27.9 mmoles) of NEt₃. This mixture is stirred at 120° C. for 24 hours. After concentrating the reaction medium to dryness, the residue obtained is taken up with AcOEt and washed with water and with a saturated NaCl solution. After drying on MgSO₄, the organic phase is concentrated to dryness. The residue obtained is purified by silica flash chromatography (CH₂Cl₂-AcOEt gradient: 100-0 to 90-10). 0.86 g of beige solid is isolated (yield: 36%).

TLC silica gel 60 F 254 Merck, CH₂Cl₂-MeOH: 95-5, Rf=0.71.

F=162° C.

$^1$H NMR (CDCl₃) ppm: 3.28 (t, 2H, J=5.18 Hz), 3.44 (s, 3H), 3.67-3.88 (m, 3H), 3.93-4.09 (m, 3H), 6.73 (s, 1H), 7.35 (d, 1H, J=7.6 Hz), 7.54 (t, 1H, J=7.6 Hz), 7.62 (t, 1H, J=7.6 Hz), 7.73 (d, 1H J=8 Hz).

MS (+ESI) m/z 401 (MH+)

Example 2

4'-Methyl-4-(2-trifluoromethyl-benzoyl)-3,4,5,6-tetrahydro-2H,4'H-[1,2']bipyrazinyl-3'-one (2)

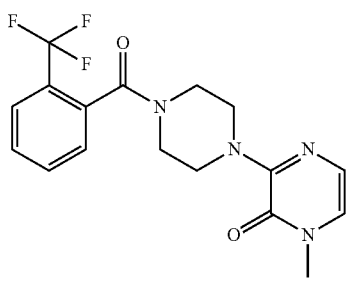 [SMILES: Cn1ccnc(N2CCN(C(=O)c3ccccc3C(F)(F)F)CC2)c1=O]

Compound 2 is prepared according to synthesis method 4: 0.46 g (1.15 mmoles) of the compound described for example 1 is placed in 5 ml of methanol in the presence of 0.15 g (1.15 mmoles) of potassium carbonate and 0.05 g of carbon-activated palladium (5%). The medium is placed under hydrogen pressure (7 bar) and left under stirring at ambient temperature for 48 hours. After filtering the reaction medium on celite, the filtrate is concentrated. The residue obtained is purified by flash chromatography ($CH_2Cl_2$-MeOH gradient: 100-0 to 98-2). 0.26 g of beige solid is obtained (yield: 62%).

TLC silica gel 60 F 254 Merck, $CH_2Cl_2$-MeOH: 95-5, Rf=0.54.

F=142° C.

$^1$H NMR ($CDCl_3$) ppm: 3.28 (t, 2H, J=5.42 Hz), 3.47 (s, 3H), 3.69 (t, 2H, J=5.42 Hz), 3.81-4.00 (m, 4H), 6.69 (d, 1H, J=4.42 Hz), 6.91 (d, 1H, J=4.42 Hz), 7.35 (d, 1H, J=7.6 Hz), 7.54 (t, 1H, J=7.6 Hz), 7.61 (t, 1H, J=7.6 Hz), 7.72 (t, 1H, J=8 Hz).

MS (+ESI) m/z 367 (MH+)

Example 3

(4-[1,2,4]Triazin-3-yl-piperazin-1-yl)-(2-trifluoromethyl-phenyl)-methanone (3)

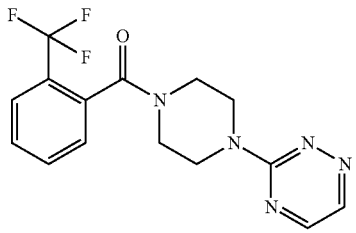 [SMILES: O=C(c1ccccc1C(F)(F)F)N1CCN(c2nccnn2)CC1]

Compound 3 is prepared according to synthesis method 2: 0.4 g (2.42 mmoles) of derivative 5a is placed in 10 ml of $CH_2Cl_2$. 0.5 ml (3.63 mmoles) of triethylamine is added. At 0° C., 0.4 ml (2.66 mmoles) of trifluoromethylbenzoyl chloride is added drop by drop, the reaction medium is stirred at ambient temperature for 18 hours. After concentrating the reaction medium to dryness, the residue obtained is taken up with AcOEt and washed with water. After drying on $MgSO_4$, the organic phase is concentrated. The residue obtained is purified by silica flash chromatography ($CH_2Cl_2$,100%). 0.72 g of yellow powder is isolated (yield: 95%).

TLC silica gel 60 F 254 Merck, $CH_2Cl_2$-MeOH-$NH_4OH$: 90-9-1, Rf=0.6.

F=104° C.

$^1$H NMR ($CDCl_3$) ppm: 3.30 (t, 2H, J=5.2 Hz), 3.82-3.92 (m, 3H), 3.97-4.10 (m, 3H), 7.37 (d, 1H, J=7.6 Hz), 7.56 (t, 1H, J=7.6 Hz), 7.64 (t, 1H, J=7.6 Hz), 7.75 (d, 1H, J=8 Hz), 8.16 (d, 1H, J=2 Hz), 8.57 (d, 1H, J=2.4 Hz).

MS (+APCI) m/z 338 (MH+)

Example 4

(5-Fluoro-2-trifluoromethyl-phenyl)-(4-[1,2,4]triazin-3-yl-piperazin-1-yl)-methanone (4)

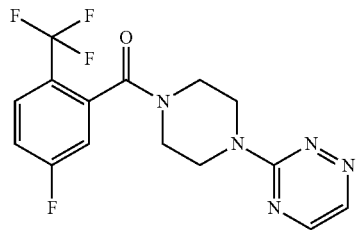 [SMILES: O=C(c1cc(F)ccc1C(F)(F)F)N1CCN(c2nccnn2)CC1]

Compound 4 is prepared from 5-fluoro-2-trifluoromethyl-benzoyl chloride and intermediate 5a according to synthesis method 2 under the operating conditions described for example 3 (67% yield).

TLC silica gel 60 F 254 Merck, $CH_2Cl_2$-MeOH-$NH_4OH$: 90-9-1, Rf=0.77.

F=122° C.

$^1$H NMR ($CDCl_3$) ppm: 3.31 (t, 2H, J=5.24 Hz), 3.83-3.92 (m, 5H), 3.95-4.07 (m, 1H), 7.07-7.10 (m, 1H), 7.22-7.23 (m, 1H), 7.74-7.77 (m, 1H), 8.16 (d, 1H, J=2.1 Hz), 8.57 (d, 1H, J=2.1 Hz).

MS (+ESI) m/z 356 (MH+)

Example 5

3-[4-(2-Trifluoromethyl-benzyl)-piperazin-1-yl]-[1,2,4]triazine (5)

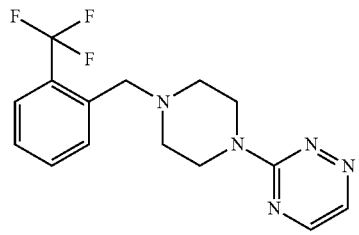 [SMILES: FC(F)(F)c1ccccc1CN1CCN(c2nccnn2)CC1]

Compound 5 is prepared from 1-bromomethyl-2-trifluoromethyl-benzene and intermediate 5a according to synthesis method 2 in refluxing toluene (33% yield).

TLC silica gel 60 F 254 Merck, $CH_2Cl_2$-MeOH-$NH_4OH$: 90-9-1, Rf=0.63.

$^1$H NMR ($CDCl_3$) ppm: 2.54-2.59 (m, 4H), 3.91 (s, 2H), 3.93-3.95 (m, 4H), 7.36 (t, 1H, J=7.6 Hz), 7.55 (t, 1H, J=7.6 Hz), 7.64 (d, 1H, J=7.84 Hz), 7.84 (d, 1H, J=7.76 Hz), 8.11 (d, 1H, J=2.2 Hz), 8.49 (d, 1H, J=2.2 Hz).

MS (+ESI) m/z 324 (MH+)

Example 6

5-Chloro-3-[4-(2-chloro-phenoxy)-piperidin-1-yl]-1-methyl-1H-pyrazin-2-one (6)

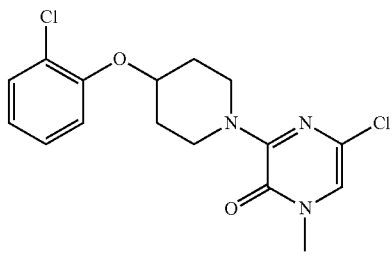 [SMILES: Cn1cc(Cl)nc(N2CCC(Oc3ccccc3Cl)CC2)c1=O]

Compound 6 is prepared from intermediate 1d according to synthesis method 1 under the operating conditions described for example 1 (49% yield).

TLC silica gel 60 F 254 Merck, CH$_2$Cl$_2$-MeOH: 95-5, Rf=0.69.

F=102° C.

$^1$H NMR (CDCl$_3$) ppm: 1.97-2.03 (m, 4H), 3.40 (s, 3H), 3.99-4.20 (m, 4H), 4.61 (m, 1H), 6.66 (s, 1H), 6.91 (t, 1H, J=7.6 Hz), 6.97 (d, 1H, J=8.1 Hz), 7.20 (t, 1H, J=7.6 Hz), 7.37 (d, 1H J=7.76 Hz).

MS (+ESI) m/z 354 (MH+)

Example 7

5-Chloro-1-methyl-3-[4-(2-trifluoromethyl-phenoxy)-piperidin-1-yl]-1H-pyrazin-2-one (7)

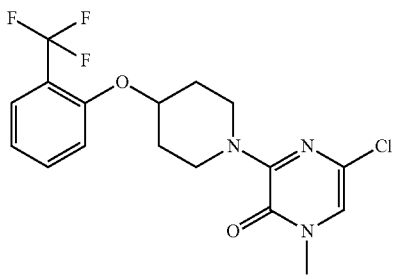 [SMILES: Cn1cc(Cl)nc(N2CCC(Oc3ccccc3C(F)(F)F)CC2)c1=O]

Compound 7 is prepared from pyrazinone 4c and intermediate 1a according to synthesis method 1 under the operating conditions described for example 1 (25% yield).

TLC silica gel 60 F 254 Merck, CH$_2$Cl$_2$-AcOEt: 90-10, Rf=0.43.

F=90° C.

$^1$H NMR (CDCl$_3$) ppm: 1.96-2.07 (m, 4H), 3.42 (s, 3H), 3.89-3.94 (m, 2H), 4.12-4.17 (m, 2H), 4.72 (m, 1H), 6.66 (s, 1H), 6.99 (m, 2H), 7.47 (t, 1H, J=7.84 Hz), 7.58 (d, 1H J=7.64 Hz).

MS (+ESI) m/z 388 (MH+)

Example 8

5-Chloro-8-[4-(2-chloro-5-trifluoromethyl-phenoxy)-piperidin-1-yl]-1-methyl-1H-pyrazin-2-one (8)

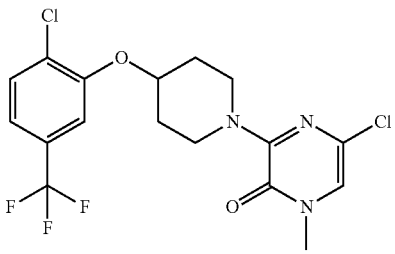 [SMILES: Cn1cc(Cl)nc(N2CCC(Oc3cc(C(F)(F)F)ccc3Cl)CC2)c1=O]

Compound 8 is prepared according to synthesis method 3: 0.2 g (0.82 mmoles) of intermediate 5g is placed in the presence of 0.17 g (0.90 mmoles) of 2-chloro-5-trifluoromethylphenol, 0.26 g (0.98 mmoles) of triphenylphosphine in 5 ml of THF. At 0° C., 0.18 ml (0.98 mmoles) of DEAD is added drop by drop. The reaction medium is heated for 8 hours at 70° C., and left under stirring at ambient temperature for 15 hours. After concentration, the residue obtained is taken up with ether and washed with a sodium hydroxide solution (1N). After drying on MgSO$_4$, the organic phase is concentrated to dryness, the residue obtained is purified by silica flash chromatography (CH$_2$Cl$_2$-AcOEt gradient: 100-0 to 95-5 for 30 min). 0.11 g of rose-pink solid is obtained (31% yield).

TLC silica gel 60 F 254 Merck, CH$_2$Cl$_2$-AcOEt: 95-5, Rf=0.58.

F=111° C.

$^1$H NMR (CDCl$_3$) ppm: 1.94-2.04 (m, 4H), 3.43 (s, 3H), 4.03-4.07 (m, 4H), 4.68 (m, 1H), 6.67 (s, 1H), 7.17 (s, 1H), 7.18 (d, 1H, J=8.1 Hz), 7.49 (d, 1H, J=8 Hz).

MS (+ESI) m/z 422 (MH+)

Example 9

5-Chloro-1-methyl-3-(4-o-tolyloxy-piperidin-1-yl)-1H-pyrazin-2-one (9)

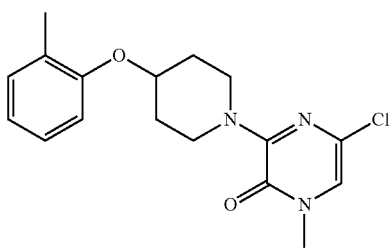 [SMILES: Cc1ccccc1OC1CCN(c2nc(Cl)cn(C)c2=O)CC1]

Compound 9 is prepared from pyrazinone 4c and intermediate 1g according to synthesis method 1 under the operating conditions described for example 1 (59% yield).

TLC silica gel 60 F 254 Merck, CH$_2$Cl$_2$-AcOEt: 95-5, Rf=0.72.

F=102° C.

$^1$H NMR (CDCl$_3$) ppm: 1.89-1.96 (m, 2H), 2.01-2.08 (m, 2H), 2.24 (s, 3H), 3.42 (s, 3H), 3.93-3.99 (m, 2H), 4.03-4.11 (m, 2H), 4.54-4.57 (m, 1H), 6.66 (s, 1H), 6.84-6.88 (m, 2H), 7.12-7.16 (m, 2H).

MS (+APCI) m/z 334 (MH+)

Example 10

1-Methyl-3-(4-o-tolyloxy-piperidin-1-yl)-1H-pyrazin-2-one (10)

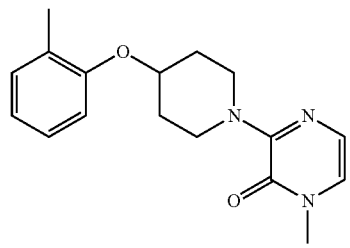 [SMILES: Cc1ccccc1OC1CCN(c2nccn(C)c2=O)CC1]

Compound 10 is prepared from the derivative described for example 9 according to synthesis method 4 under the operating conditions described for example 2, using a (1/1) methanol/dichloromethane mixture as a solvent (61% yield).

TLC silica gel 60 F 254 Merck, $CH_2Cl_2$-AcOEt: 95-5, Rf=0.28.

F=97° C.

$^1$H NMR (CDCl$_3$) ppm: 1.89-1.96 (m, 2H), 2.03-2.09 (m, 2H), 2.24 (s, 3H), 3.63 (s, 3H), 3.73-3.79 (m, 2H), 3.98-4.04 (m, 2H), 4.53-4.56 (m, 1H), 6.63 (d, 1H, J=4.4 Hz), 6.84-6.87 (m, 2H), 6.91 (d, 1H, J=4.4 Hz), 7.12-7.16 (m, 2H).

MS (+ESI) m/z 300 (MH+)

Example 11

1-Methyl-3-[4-(2-trifluoromethyl-phenoxy)-piperidin-1-yl]-1H-pyrazin-2-one (11)

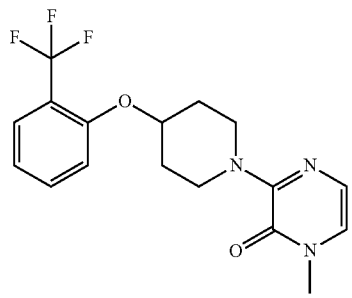 [SMILES: Cn1ccnc(N2CCC(Oc3ccccc3C(F)(F)F)CC2)c1=O]

Compound 11 is prepared from the derivative described for example 7 according to synthesis method 4 under the operating conditions described for example 2, using a (1/1) methanol/dichloromethane mixture as a solvent (70% yield).

TLC silica gel 60 F 254 Merck, $CH_2Cl_2$-AcOEt: 95-5, Rf=0.49.

F=90° C.

$^1$H NMR (CDCl$_3$) ppm: 1.94-2.10 (m, 4H), 3.46 (s, 3H), 3.86-3.96 (m, 4H), 4.68-4.73 (m, 1H), 6.63 (d, 1H, J=4.4 Hz), 6.91 (d, 1H, J=4.4 Hz), 6.96-7.02 (m, 2H), 7.47 (t, 1H, J=7.6 Hz), 7.58 (d, 1H, J=7.6 Hz).

MS (+ESI) m/z 354 (MH+)

Example 12

5-Chloro-3-[4-(2-chloro-5-fluoro-phenoxy)-piperidin-1-yl]-1-methyl-1H-pyrazin-2-one (12)

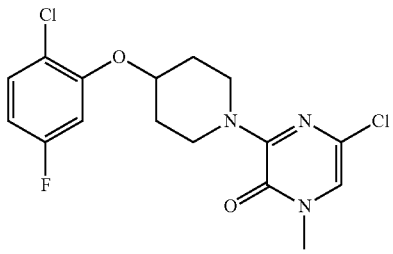 [SMILES: Cn1cc(Cl)nc(N2CCC(Oc3cc(F)ccc3Cl)CC2)c1=O]

Compound 12 is prepared from pyrazinone 4c and intermediate 1c according to synthesis method 1 under the operating conditions described for example 1 (38% yield).

TLC silica gel 60 F 254 Merck, $CH_2Cl_2$-AcOEt: 95-5, Rf=0.67.

F=84° C.

$^1$H NMR (CDCl$_3$) ppm: 1.92-2.08 (m, 4H), 3.43 (s, 3H), 4.03-4.06 (m, 4H), 4.56-4.61 (m, 1H), 6.67 (s, 1H), 6.62-6.72 (m, 2H), 7.29-7.33 (m, 1H).

MS (+APCI) m/z 372 (MH+)

Example 13

3-[4-(2-Chloro-phenoxy)-piperidin-1-yl]-[1,2,4]triazine (13)

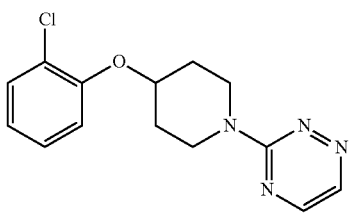 [SMILES: Clc1ccccc1OC1CCN(c2nccnn2)CC1]

Compound 13 is prepared from 2-chlorophenol and intermediate 5e according to synthesis method 3 under the operating conditions described for example 8 (50% yield).

TLC silica gel 60 F 254 Merck, $CH_2Cl_2$-AcOEt: 95-5, Rf=0.25.

F=67° C.

$^1$H NMR (DMSO-d$_6$) ppm: 1.69-1.77 (m, 2H), 1.97-2.04 (m, 2H), 3.78-3.84 (m, 2H), 4.06-4.12 (m, 2H), 4.79-4.84 (m, 1H), 6.95-7.00 (m, 1H), 7.28-7.33 (m, 2H), 7.44 (d, 1H, J=8 Hz), 8.63 (d, 1H, J=2.2 Hz), 8.34 (d, 1H, J=2.2 Hz).

MS (+ESI) m/z 291 (MH+)

Example 14

3-[4-(2-Trifluoromethyl-phenoxy)-piperidin-1-yl]-[1,2,4]triazine (14)

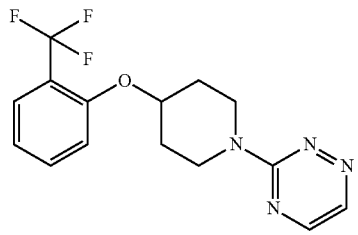 [SMILES: FC(F)(F)c1ccccc1OC1CCN(c2nccnn2)CC1]

Compound 14 is prepared from 2-trifluoromethylphenol and intermediate 5e according to synthesis method 3 under the operating conditions described for example 8 (30% yield).

TLC silica gel 60 F 254 Merck, CH$_2$Cl$_2$-AcOEt: 95-5, Rf=0.33.

F=70° C.

$^1$H NMR (CDCl$_3$) ppm: 1.96-2.05 (m, 4H), 3.88-3.95 (m, 2H), 4.19-4.24 (m, 2H), 4.78-4.82 (m, 1H), 6.99-7.04 (m, 2H), 7.49 (t, 1H, J=7.2 Hz), 7.60 (d, 1H, J=7.6 Hz), 8.12 (d, 1H, J=2.2 Hz), 8.49 (d, 1H, J=2 Hz).

MS (+ESI) m/z 325 (MH+)

Example 15

3-[4-(2-Chloro-5-fluoro-phenoxy)-piperidin-1-yl]-5-phenyl-[1,2,4]triazine (15)

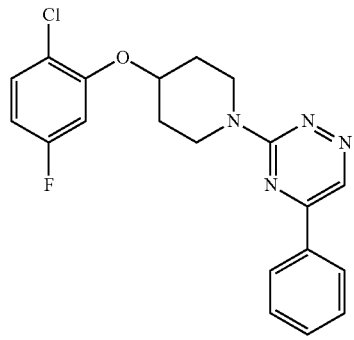 [SMILES: Fc1ccc(Cl)c(OC2CCN(c3nncc(-c4ccccc4)n3)CC2)c1]

Compound 15 is prepared from 2-chloro-5-trifluoromethylphenol and intermediate 5f according to synthesis method 3 under the operating conditions described for example 8 (28% yield).

TLC silica gel 60 F 254 Merck, CH$_2$Cl$_2$-MeOH: 95-5, Rf=0.63.

F=61° C.

$^1$H NMR (CDCl$_3$) ppm: 1.97-2.07 (m, 4H), 4.18-4.23 (m, 4H), 4.64-4.69 (m, 1H), 6.66 (t, 1H, J=8 Hz), 6.75 (d, 1H, J=7.2 Hz), 7.33 (t, 1H, J=8.8 Hz), 7.50-7.58 (m, 3H), 8.10 (d, 2H, J=8 Hz), 9.00 (s, 1H).

MS (+ESI) m/z 385 (MH+)

Example 16

5-Phenyl-3-[4-(2-trifluoromethyl-phenoxy)-piperidin-1-yl]-[1,2,4]triazine (16)

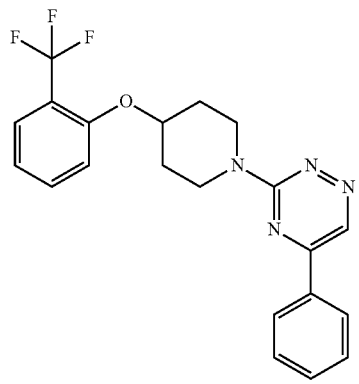 [SMILES: FC(F)(F)c1ccccc1OC1CCN(c2nncc(-c3ccccc3)n2)CC1]

Compound 16 is prepared from 2-trifluoromethylphenol and intermediate 5f according to synthesis method 3 under the operating conditions described for example 8 (24% yield).

TLC silica gel 60 F 254 Merck, CH$_2$Cl$_2$-MeOH: 95-5, Rf=0.61.

$^1$H NMR (CDCl$_3$) ppm: 2.02-2.06 (m, 4H), 3.99-4.05 (m, 2H), 4.28-4.33 (m, 2H), 4.78-4.83 (m, 1H), 6.93-7.06 (m, 2H), 7.48-7.61 (m, 5H), 8.10 (d, 2H, J=8 Hz), 8.99 (s, 1H).

MS (+ESI) m/z 401 (MH+)

Example 17

3-[4-(2-Chloro-5-trifluoromethyl-phenoxy)-piperidin-1-yl]-[1,2,4]triazine (17)

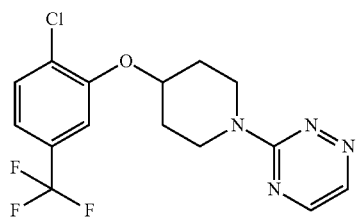 [SMILES: FC(F)(F)c1ccc(Cl)c(OC2CCN(c3nccnn3)CC2)c1]

Compound 17 is prepared from 2-chloro-5-trifluoromethylphenol and intermediate 5e according to synthesis method 3 under the conditions described for example 8 (55% yield).

TLC silica gel 60 F 254 Merck, CH$_2$Cl$_2$-MeOH: 95-5, Rf=0.74.

F=66° C.

$^1$H NMR (CDCl$_3$) ppm: 1.96-2.04 (m, 4H), 4.02-4.12 (m, 4H), 4.73-4.77 (m, 1H), 7.19-7.21 (m, 2H, J=7.2 Hz), 7.51 (d, 1H, J=8 Hz), 8.13 (d, 1H, J=2.4 Hz), 8.51 (d, 1H, J=2.4 Hz).

MS (+ESI) m/z 359 (MH+)

Example 18

3-[4-(2-Chloro-5-fluoro-phenoxy)-piperidin-1-yl]-[1,2,4]triazine (18)

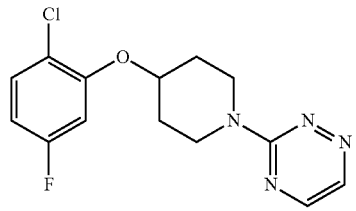 [SMILES: Fc1ccc(Cl)c(OC2CCN(c3nccnn3)CC2)c1]

Compound 18 is prepared from 2-chloro-5-fluorophenol and intermediate 5e according to synthesis method 3 under the operating conditions described for example 8 (57% yield).

TLC silica gel 60 F 254 Merck, $CH_2Cl_2$-MeOH: 95-5, Rf=0.57.

$^1$H NMR (CDCl$_3$) ppm: 1.95-2.02 (m, 4H), 4.04-4.11 (m, 4H), 4.63-4.67 (m, 1H), 6.66 (td, 1H, J=8.4 Hz and J=2.4 Hz), 6.73 (dd, 1H, J=10.4 Hz and J=2.8 Hz), 7.33 (m, 1H), 8.13 (d, 1H, J=2.4 Hz), 8.50 (d, 1H, J=2 Hz).

MS (+APCI) m/z 308 (MH+)

Example 19

3-[4-(2-Chloro-5-trifluoromethyl-phenoxy)-piperidin-1-yl]-5,6-dimethyl-[1,2,4]triazine (19)

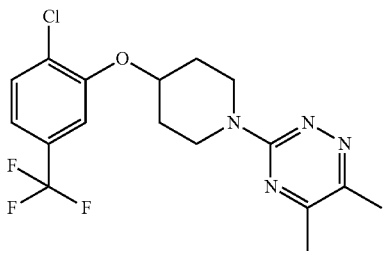 [SMILES: Cc1nnc(N2CCC(Oc3cc(C(F)(F)F)ccc3Cl)CC2)nc1C]

Compound 19 is prepared from derivative 3a and intermediate 1b according to synthesis method 1, with no base, refluxing THF, under the operating conditions described for example 1 (yield: 55%).

TLC silica gel 60 F 254 Merck, $CH_2Cl_2$-AcOEt: 50-50, Rf=0.57.

$^1$H NMR (DMSO-d$_6$) ppm: 1.63-1.74 (m, 2H), 1.93-2.04 (m, 2H), 2.35 (s, 3H), 2.42 (s, 3H), 3.68-3.77 (m, 2H), 4.02-4.12 (m, 2H), 4.97-5.05 (m, 1H), 7.34 (d, 1H, J=8.4 Hz), 7.62 (s, 1H), 7.69 (d, 1H, J=8.4 Hz).

MS (+ESI) m/z 387 (MH+)

Example 20

3-[4-(2-Chloro-5-trifluoromethyl-phenoxy)-piperidin-1-yl]-5,6-diphenyl-[1,2,4]triazine (20)

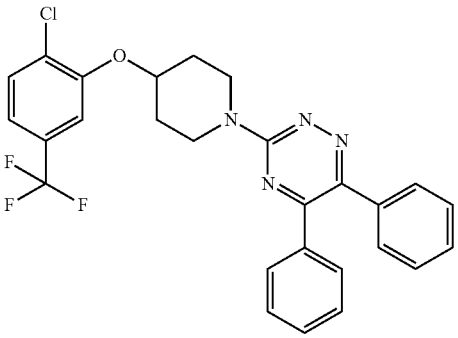 [SMILES: FC(F)(F)c1ccc(Cl)c(OC2CCN(c3nnc(-c4ccccc4)c(-c4ccccc4)n3)CC2)c1]

Compound 20 is prepared from derivative 3b and intermediate 1b according to synthesis method 1 under the operating conditions described for example 19 (yield: 58%).

TLC silica gel 60 F 254 Merck, $CH_2Cl_2$-AcOEt: 50-50, Rf=0.82.

F=75° C.

$^1$H NMR (DMSO-d$_6$) ppm: 1.75-1.86 (m, 2H), 2.03-2.15 (m, 2H), 3.88-3.99 (m, 2H), 4.17-4.28 (m, 2H), 5.04-5.12 (m, 1H), 7.30-7.39 (m, 8H), 7.40-7.47 (m, 3H), 7.66 (s, 1H), 7.71 (d, 1H, J=8.4 Hz).

MS (+ESI) m/z 511 (MH+)

Example 21

3-[4-(2-Chloro-5-trifluoromethyl-phenoxy)-piperidin-1-yl]-5,6,7,8-tetrahydro-benzo[1,2,4]triazine (21)

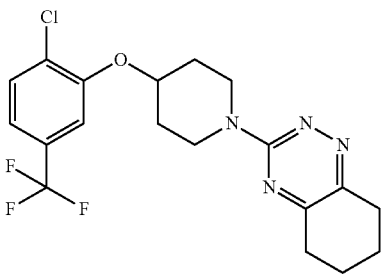 [SMILES: FC(F)(F)c1ccc(Cl)c(OC2CCN(c3nnc4c(n3)CCCC4)CC2)c1]

Compound 21 is prepared from derivative 3c and intermediate 1b according to synthesis method 1 under the operating conditions described for example 19 (yield: 33%).

TLC silica gel 60 F 254 Merck, $CH_2Cl_2$-AcOEt: 50-50, Rf=0.58.

F=153° C.

$^1$H NMR (DMSO-d$_6$) ppm: 1.63-1.86 (m, 6H), 1.94-2.03 (m, 2H), 2.71 (t, 2H, J=5.6 Hz), 2.85 (t, 2H, J=5.6 Hz) 3.62-3.78 (m, 2H), 4.02-4.11 (m, 2H), 4.98-5.05 (m, 1H), 7.34 (d, 1H, J=8.4 Hz), 7.62 (s, 1H), 7.69 (d, 1H, J=8.4 Hz).

MS (+ESI) m/z 413 (MH+)

Example 22

3-[4-(2-Chloro-5-trifluoromethyl-phenoxy)-piperidin-1-yl]-6-methyl-5-(3-trifluoromethyl-phenyl)-[1,2,4]triazine (22)

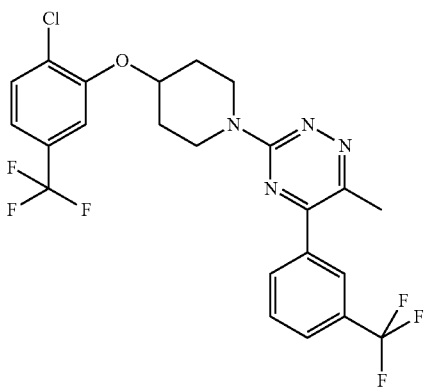 [SMILES: Cc1nnc(N2CCC(Oc3cc(C(F)(F)F)ccc3Cl)CC2)nc1-c1cccc(C(F)(F)F)c1]

Compound 22 is prepared from derivative 3d and intermediate 1b according to synthesis method 1 under the operating conditions described for example 19 (yield: 62%).

TLC silica gel 60 F 254 Merck, CH$_2$Cl$_2$-AcOEt: 50-50, Rf=0.69.

$^1$H NMR (DMSO-d$_5$) ppm: 1.70-1.82 (m, 2H), 2.00-2.10 (m, 2H), 2.42 (s, 3H), 3.82-3.93 (m, 2H), 4.11-4.21 (m, 2H), 5.03-5.10 (m, 1H), 7.35 (d, 1H, J=8.2 Hz), 7.65 (s, 1H), 7.69-7.77 (m, 2H), 7.83 (d, 1H, J=8.0 Hz), 7.95 (d, 1H, J=7.5 Hz), 7.98 (s, 1H).

MS (+ESI) m/z 517 (MH+)

Example 23

3-[4-(2-Chloro-5-trifluoromethyl-phenoxy)-piperidin-1-yl]-5,6-di-furan-2-yl-[1,2,4]triazine (23)

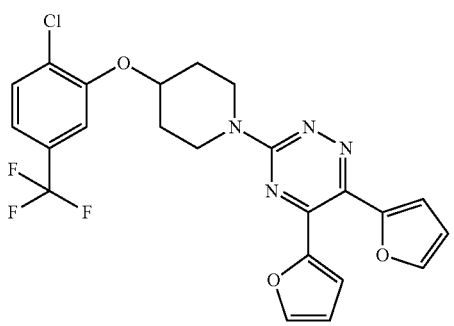 [SMILES: FC(F)(F)c1ccc(Cl)c(OC2CCN(c3nnc(-c4ccco4)c(-c4ccco4)n3)CC2)c1]

Compound 23 is prepared from derivative 3e and intermediate 1b according to synthesis method 1 under the operating conditions described for example 19 (yield: 63%).

TLC silica gel 60 F 254 Merck, CH$_2$Cl$_2$-AcOEt: 50-50, Rf=0.63.

$^1$H NMR (DMSO-d$_6$) ppm: 1.74-1.86 (m, 2H), 2.02-2.13 (m, 2H), 3.89-4.00 (m, 2H), 4.13-4.24 (m, 2H), 5.02-5.11 (m, 1H), 6.56 (d, 1H, J=3.4 Hz), 6.67-6.72 (m, 2H), 6.81 (d, 1H, J=3.3 Hz), 7.35 (d, 1H, J=8.4 Hz), 7.66 (s, 1H), 7.72 (d, 1H, J=8.1 Hz), 7.86 (s, 1H), 7.97 (s, 1H).

MS (+EST) m/z 491 (MH+)

Example 24

3-[4-(2-Chloro-5-trifluoromethyl-phenoxy)-piperidin-1-yl]-5,6-di-pyridin-2-yl-[1,2,4]triazine (24)

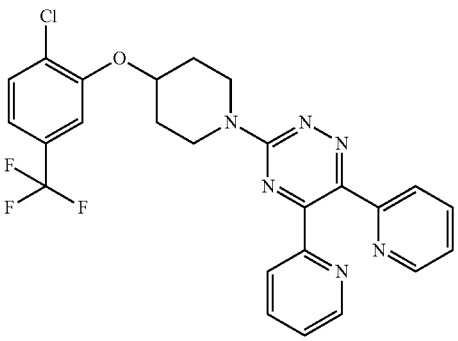 [SMILES: FC(F)(F)c1ccc(Cl)c(OC2CCN(c3nnc(-c4ccccn4)c(-c4ccccn4)n3)CC2)c1]

Compound 24 is prepared from derivative 3f and intermediate 1b according to synthesis method 1 under the operating conditions for example 19 (yield: 84%).

TLC silica gel 60 F 254 Merck, CH$_2$Cl$_2$-AcOEt: 50-50, Rf=0.21.

F=130° C.

$^1$H NMR (DMSO-d$_6$) ppm: 1.77-1.88 (m, 2H), 2.05-2.15 (m, 2H), 3.93-4.04 (m, 2H), 4.18-4.28 (m, 2H), 5.05-5.13 (m, 1H), 7.26-7.31 (m, 1H), 7.33-7.42 (m, 2H), 7.67 (s, 1H), 7.71 (d, 1H, J=8.4 Hz), 7.86-7.96 (m, 4H), 8.24 (d, 1H, J=4.8 Hz), 8.30 (d, 1H, J=4.8 Hz).

MS (+ESI) m/z 513 (MH+)

Example 25

3-[4-(2-Chloro-5-fluoro-phenoxy)-piperidin-1-yl]-5-methyl-[1,2,4]triazine (25)

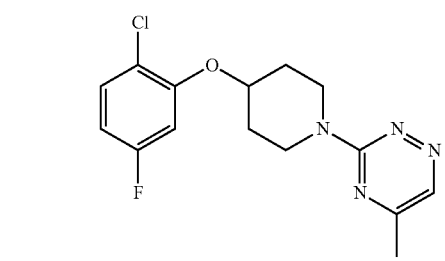 [SMILES: Cc1cnnc(N2CCC(Oc3cc(F)ccc3Cl)CC2)n1]

Compound 25 is prepared from triazine 2c and intermediate 1c according to synthesis method 1 under the operating conditions for example 1 (12% yield).

TLC silica gel 60 F 254 Merck, CH$_2$Cl$_2$-AcOEt: 95-5, Rf=0.28.

F=92° C.

$^1$H NMR (CDCl$_3$) ppm: 1.92-2.05 (m, 4H), 2.36 (s, 3H), 4.02-4.10 (m, 4H), 4.62-4.65 (m, 1H), 6.63-6.69 (m, 1H), 6.70-6.75 (m, 1H), 7.30-7.35 (m, 1H), 8.40 (s, 1H).

MS (+ESI) m/z 323 (MH+)

Example 26

5-Methyl-3-(4-o-tolyloxy-piperidin-1-yl)-[1,2,4]triazine (26)

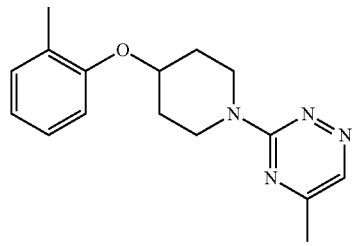 [SMILES: Cc1cnnc(N2CCC(Oc3ccccc3C)CC2)n1]

Compound 26 is prepared from triazine 2c and intermediate 1g according to synthesis method 1 under the operating conditions described for example 1 (22% yield).

TLC silica gel 60 F 254 Merck, $CH_2Cl_2$-AcOEt: 95-5, Rf=0.27.

F=100° C.

$^1$H NMR ($CDCl_3$) ppm: 1.87-1.95 (m, 2H), 1.98-2.05 (m, 2H), 2.25 (s, 3H), 2.35 (s, 3H), 3.94-4.00 (m, 2H), 4.07-4.13 (m, 2H), 4.62-4.65 (m, 1H), 6.87 (m, 2H), 7.16 (m, 2H), 8.39 (s, 1H).

MS (+ESI) m/z 285 (MH+)

Example 27

3-[4-(2-Chloro-5-trifluoromethyl-phenoxy)-piperidin-1-yl]-5-methyl-[1,2,4]triazine (27)

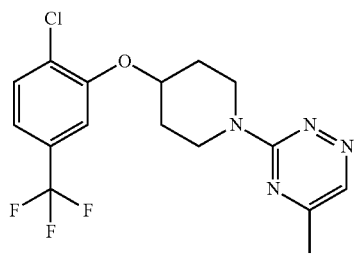 [SMILES: Cc1cnnc(N2CCC(Oc3cc(C(F)(F)F)ccc3Cl)CC2)n1]

Compound 27 is prepared from triazine 2c and intermediate 1b according to synthesis method 1 under the operating conditions described for example 1 (11% yield).

TLC silica gel 60 F 254 Merck, $CH_2Cl_2$-AcOEt: 95-5, Rf=0.3.

F=68° C.

$^1$H NMR ($CDCl_3$) ppm: 1.92-2.04 (m, 4H), 2.36 (s, 3H), 4.04-4.12 (m, 4H), 4.71-4.75 (m, 1H), 7.18-7.20 (m, 2H), 7.16 (d, 1H, J=8.8 Hz), 8.41 (s, 1H).

MS (+ESI) m/z 373 (MH+)

Example 28

3-[4-(2-Chloro-phenoxy)-piperidin-1-yl]-5-methyl-[1,2,4]triazine (28)

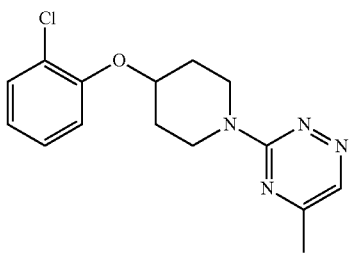 [SMILES: Cc1cnnc(N2CCC(Oc3ccccc3Cl)CC2)n1]

Compound 28 is prepared from triazine 2c and intermediate 1d according to synthesis method 1 under the operating conditions described for example 1 (10% yield).

TLC silica gel 60 F 254 Merck, $CH_2Cl_2$-AcOEt: 95-5, Rf=0.23.

F=118° C.

$^1$H NMR ($CDCl_3$) ppm: 1.92-2.04 (m, 4H), 2.35 (s, 3H), 3.98-4.04 (m, 2H), 4.09-4.15 (m, 2H), 4.64-4.67 (m, 1H), 6.93 (t, 1H, J=7.6 Hz), 7.00 (d, 1H, J=8 Hz), 7.22 (t, 1H, J=7.6 Hz), 7.39 (d, 1H, J=8 Hz), 8.39 (s, 1H).

MS (+ESI) m/z 305 (MH+)

Example 29

3-(4-o-Tolyloxy-piperidin-1-yl)-[1,2,4]triazine (29)

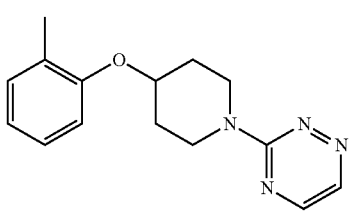 [SMILES: Cc1ccccc1OC1CCN(c2nccnn2)CC1]

Compound 29 is prepared from triazine 2a and intermediate 1g according to synthesis method 1 under the operating conditions described for example 1 (36% yield).

TLC silica gel 60 F 254 Merck, $CH_2Cl_2$-AcOEt: 95-5, Rf=0.22.

$^1$H NMR ($CDCl_3$) ppm: 1.90-2.06 (m, 4H), 2.26 (s, 3H), 3.98-4.12 (m, 4H), 4.65-4.68 (m, 1H), 6.86-6.90 (m, 2H), 7.16 (m, 2H), 8.12 (d, 1H, J=2 Hz), 8.49 (d, 1H, J=2.4 Hz).

MS (+ESI) m/z 271 (MH+)

Example 30

3-[4-(2-Chloro-5-fluoro-phenoxy)-piperidin-1-yl]-6-methyl-[1,2,4]triazine (30)

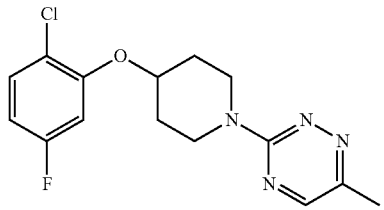 [SMILES: Cc1cnc(N2CCC(Oc3cc(F)ccc3Cl)CC2)nn1]

Compound 30 is prepared from triazine 2j and intermediate 1c according to synthesis method 1 under the operating conditions described for example 1 (8% yield).

TLC silica gel 60 F 254 Merck, $CH_2Cl_2$-AcOEt: 90-10, Rf=0.28.

$^1$H NMR (CDCl$_3$) ppm: 1.91-2.05 (m, 4H), 2.51 (s, 3H), 3.96-4.10 (m, 4H), 4.60-4.63 (m, 1H), 6.65 (td, 1H, J=8.8 Hz and J=2.8 Hz), 6.72 (dd, 1H, J=10 Hz and J=2.8 Hz), 7.30-7.34 (m, 1H), 8.03 (s, 1H).

MS (+ESI) m/z 323 (MH+)

Example 31

6-Methyl-3-(4-o-tolyloxy-piperidin-1-yl)-[1,2,4]triazine (31)

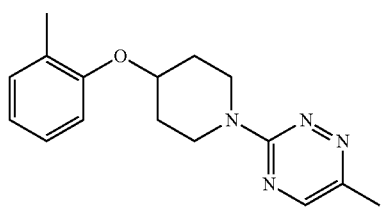 [SMILES: Cc1cnc(N2CCC(Oc3ccccc3C)CC2)nn1]

Compound 31 is prepared from triazine 2j and intermediate 1g according to synthesis method 1 under the operating conditions described for example 1 (6% yield).

TLC silica gel 60 F 254 Merck, $CH_2Cl_2$-AcOEt: 90-10, Rf=0.27.

$^1$H NMR (CDCl$_3$) ppm: 1.87-1.93 (m, 2H), 1.98-2.04 (m, 2H), 2.25 (s, 3H), 2.51 (s, 3H), 3.89-3.95 (m, 2H), 4.04-4.10 (m, 2H), 4.60-4.64 (m, 1H), 6.87 (m, 2H), 7.15 (m, 2H), 8.02 (s, 1H).

MS (+ESI) m/z 285 (MH+)

Example 32

3-[4-(2-Chloro-5-nitro-phenoxy)-piperidin-1-yl]-[1,2,4]triazine (32)

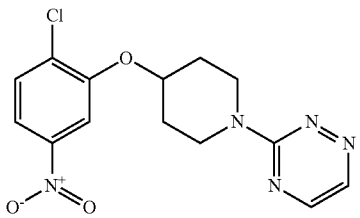 [SMILES: O=[N+]([O-])c1ccc(Cl)c(OC2CCN(c3nccnn3)CC2)c1]

Compound 32 is prepared from 2-chloro-5-nitrophenol and intermediate 5e according to synthesis method 3 under the operating conditions described for example 8 (54% yield).

TLC silica gel 60 F 254 Merck, $CH_2Cl_2$-AcOEt: 95-5, Rf=0.26.

$^1$H NMR (CDCl$_3$) ppm: 1.97-2.12 (m, 4H), 4.04-4.16 (m, 4H), 4.82-4.85 (m, 1H), 7.56 (d, 1H, J=8.4 Hz), 7.83 (d, 1H, 7.6 Hz), 7.84 (s, 1H), 8.14 (d, 1H, J=2 Hz), 8.52 (d, 1H, J=2 Hz).

MS (+ESI) m/z 336 (MH+)

Example 33

3-[4-(2-Bromo-4,5-difluoro-phenoxy)-piperidin-1-yl]-[1,2,4]triazine (33)

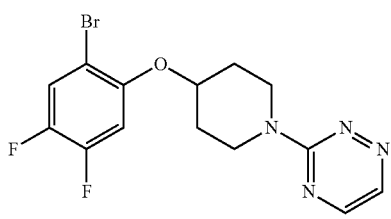 [SMILES: Fc1cc(Br)c(OC2CCN(c3nccnn3)CC2)cc1F]

Compound 33 is prepared from 2-bromo-4,5-difluoro-phenol and intermediate 5e according to the synthesis method 3 under the operating conditions described for example 8 (41% yield).

TLC silica gel 60 F 254 Merck, $CH_2Cl_2$-AcOEt: 95-5, Rf=0.28.

$^1$H NMR (CDCl$_3$) ppm: 1.93-2.03 (m, 4H), 4.01-4.14 (m, 4H), 4.56-4.62 (m, 1H), 6.80-6.85 (m, 1H), 7.39-7.44 (m, 1H), 8.13 (d, 1H, J=2 Hz), 8.51 (d, 1H, J=2 Hz).

MS (+ESI) m/z 370 (MH+)

Example 34

3-[4-(3-Fluoro-5-trifluoromethyl-phenoxy)-piperidin-1-yl]-[1,2,4]triazine (34)

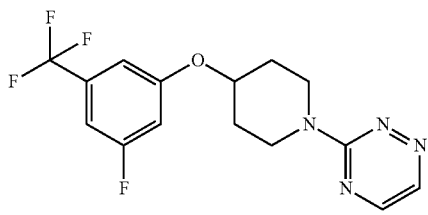 [SMILES: Fc1cc(OC2CCN(c3nccnn3)CC2)cc(C(F)(F)F)c1]

Compound 34 is prepared from 3-fluoro-5-trifluoromethyl-phenol and intermediate 5e according to synthesis method 3 under the operating conditions described for example 8 (9% yield).

TLC silica gel 60 F 254 Merck, $CH_2Cl_2$-AcOEt: 95-5, Rf=0.32.

$^1$H NMR (CDCl$_3$) ppm: 1.86-1.93 (m, 2H), 2.03-2.09 (m, 2H), 3.93-3.98 (m, 2H), 4.13-4.18 (m, 2H), 4.63-4.66 (m, 1H), 6.82 (d, 1H, J=10.4 Hz), 6.94 (d, 1H, J=8.4 Hz), 6.98 (s, 1H), 8.14 (d, 1H, J=2 Hz), 8.52 (d, 1H, J=2 Hz).

MS (+ESI) m/z 343 (MH+)

Example 35

3-[4-(2-Nitro-phenoxy)-piperidin-1-yl]-[1,2,4]triazine (35)

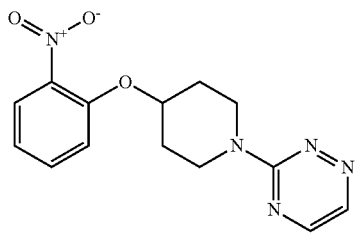 [SMILES: O=[N+]([O-])c1ccccc1OC1CCN(c2nccnn2)CC1]

Compound 35 is prepared from 2-nitro-phenol and intermediate 5e according to synthesis method 3 under the operating conditions described for example 8 (36% yield).

TLC silica gel 60 F 254 Merck, $CH_2Cl_2$-AcOEt: 95-5, Rf=0.19.

$^1$H NMR (CDCl$_3$) ppm: 1.99-2.04 (m, 4H), 3.95-4.01 (m, 2H), 4.15-4.20 (m, 2H), 4.80-4.85 (m, 1H), 7.05 (t, 1H, J=7.6 Hz), 7.13 (d, 1H, J=8.4 Hz), 7.53 (t, 1H, J=8.4 Hz), 7.84 (d, 1H, J=8 Hz), 8.12 (d, 1H, J=2 Hz), 8.50 (d, 1H, J=2 Hz).

MS (+ESI) m/z 302 (MH+)

Example 36

1-[1,2,4]Triazin-3-yl-piperidin-4-yl)-(2-trifluoromethyl-phenyl)-amine (36)

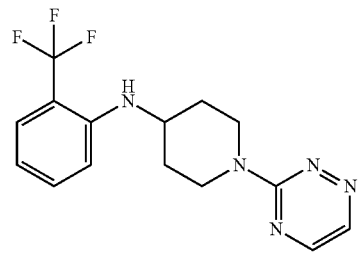 [SMILES: FC(F)(F)c1ccccc1NC1CCN(c2nccnn2)CC1]

Compound 36 is prepared according to synthesis method 3: 0.5 g (2.78 mmoles) of intermediate 5b is placed in 10 ml of toluene in the presence of 0.31 g (3.25 mmoles) of sodium tert-butoxide, 0.011 g (1.16 mmoles) tris(dibenzylidene-acetone) dipalladium, 0.021 g (3.45 mmoles) of bis-diphenylphosphino-1,1'-binaphthyl and 0.52 g (2.32 mmoles) of 2-trifluoromethyl-bromo-benzene. The medium is heated to 110° C. for 40 hours. After filtering the medium on celite, the filtrate is concentrated to dryness. The residue obtained is purified by silica flash chromatography ($CH_2Cl_2$-AcOEt gradient: 100-0 to 95-5 for 30 min). 0.19 g of rose-pink solid is obtained (25% yield).

TLC silica gel 60 F 254 Merck, $CH_2Cl_2$-AcOEt: 95-5, Rf=0.29.

F=80° C.

$^1$H NMR (CDCl$_3$) ppm: 1.49-1.59 (m, 2H), 2.17-2.21 (m, 2H), 3.31-3.38 (m, 2H), 3.69-3.76 (m, 1H), 4.23-4.26 (m, 1H), 4.67-4.71 (m, 2H), 6.73 (t, 1H, J=7.6 Hz), 6.82 (d, 1H, J=8.4 Hz), 7.38 (t, 1H, J=8 Hz), 7.45 (d, 1H, J=7.6 Hz), 8.13 (d, 1H, J=2.4 Hz), 8.51 (d, 1H, J=2.4 Hz).

MS (+ESI) m/z 324 (MH+)

Example 37

3-[4-(2-Chloro-5-trifluoromethyl-phenoxy)-3-methyl-piperidin-1-yl]-[1,2,4]triazine (37)

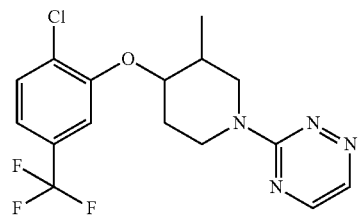 [SMILES: CC1CN(c2nccnn2)CCC1Oc1cc(C(F)(F)F)ccc1Cl]

Compound 37 is prepared from 2-chloro-5-trifluoromethylphenol and intermediate 5c according to synthesis method 3 under the operating conditions described for example 8 (38% yield).

TLC silica gel 60 F 254 Merck, $CH_2Cl_2$-MeOH: 95-5, Rf=0.84.

$^1$H NMR (CDCl$_3$) ppm: 1.12 (d, 3H, J=6.8 Hz), 2.07-2.17 (m, 2H), 3.46-3.53 (m, 2H), 4.55-4.65 (m, 3H), 7.17-7.19 (m, 2H), 7.49-7.52 (m, 1H), 8.12-8.14 (m, 1H), 8.49-8.51 (m, 1H).

MS (+ESI) m/z 373 (MH+)

Example 38

3-[4-(2,5-Dichloro-phenoxy)-3-methyl-piperidin-1-yl]-[1,2,4]triazine (38)

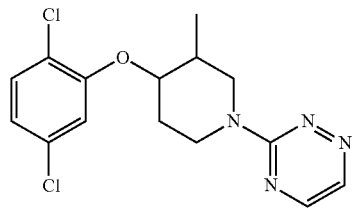 [SMILES: CC1CN(c2nccnn2)CCC1Oc1cc(Cl)ccc1Cl]

Compound 38 is prepared from 2,5-dichlorophenol and intermediate 5c according to synthesis method 3 under the operating conditions described for example 8 (37% yield).

TLC silica gel 60 F 254 Merck, $CH_2Cl_2$-MeOH: 95-5, Rf-0.85.

$^1$H NMR ($CDCl_3$) ppm: 1.12 (d, 3H, J=7.2 Hz), 2.06-2.18 (m, 2H), 3.46-3.53 (m, 2H), 4.53-4.57 (m, 3H), 6.87-6.91 (m, 1H), 6.95-6.96 (m, 1H), 7.29-7.32 (m, 1H), 8.11-8.13 (m, 1H), 8.48-8.50 (m, 1H).

MS (+ESI) m/z 339 (MH+)

Example 39

5-[4-(2-Chloro-5-trifluoromethyl-phenoxy)-piperidin-1-yl]-2-methyl-2H-pyridazin-3-one (39)

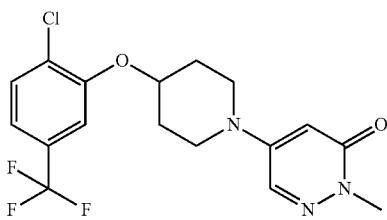 [SMILES: Cn1ncc(N2CCC(Oc3cc(C(F)(F)F)ccc3Cl)CC2)cc1=O]

Compound 39 is prepared from derivative 4a and intermediate 1b according to synthesis method 1, using ethanol as a solvent in a microwave field at 120° C. for 20 min, under the operating conditions described for example 1 (yield: 19%).

TLC silica gel 60 F 254 Merck, AcOEt, Rf=0.24.

F=130° C.

$^1$H NMR (DMSO-$d_6$) ppm: 1.64-1.75 (m, 2H), 1.93-2.03 (m, 2H), 3.32-3.41 (m, 2H), 3.51 (s, 3H), 3.55-3.65 (m, 2H), 3.92-5.00 (m, 1H), 5.92 (d, 1H, J=2.8 Hz), 7.33 (dd, 1H, J=8.0 Hz, J=1.2 Hz), 7.61 (d, 1H, J=1.2 Hz), 7.69 (d, 1H, J=8.4 Hz), 7.97 (d, 1H, J=2.8 Hz).

MS (+ESI) m/z 388 (MH+)

Example 40

4-[4-(2-Chloro-5-trifluoromethyl-phenoxy)-piperidin-1-yl]-2-methyl-2H-pyridazin-3-one (40)

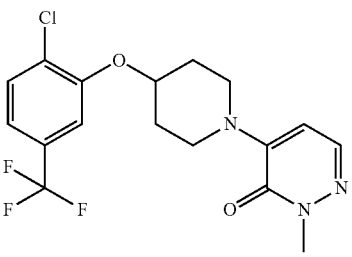 [SMILES: Cn1nccc(N2CCC(Oc3cc(C(F)(F)F)ccc3Cl)CC2)c1=O]

Compound 40 is prepared from derivative 4b and intermediate 1b according to synthesis method 1, using refluxing acetonitrile as a solvent, under the operating conditions described for example 1 (yield: 87%).

TLC silica gel 60 F 254 Merck, Petroleum-AcOEt: 60-40, Rf=0.35.

F=121° C.

$^1$H NMR (DMSO-$d_6$) ppm: 1.69-1.81 (m, 2H), 1.96-2.07 (m, 2H), 3.36-3.47 (m, 2H), 3.61 (s, 3H), 3.66-3.76 (m, 2H), 4.91-4.99 (m, 1H), 6.55 (d, 1H, J=4.9 Hz), 7.33 (d, 1H, J=8.6 Hz), 7.61 (s, 1H), 7.64 (d, 1H, J=4.8 Hz), 7.69 (d, 1H, J=8.0 Hz).

MS (+EST) m/z 388 (MH+)

Example 41

3-[3-(2-Chloro-5-trifluoromethyl-phenoxymethyl)-azetidin-1-yl]-[1,2,4]triazine (41)

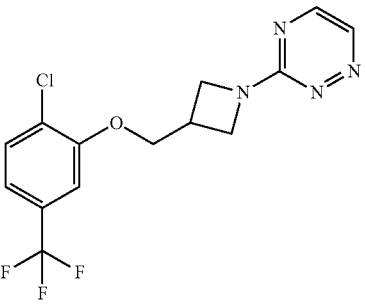 [SMILES: FC(F)(F)c1ccc(Cl)c(OCC2CN(c3nccnn3)C2)c1]

Compound 41 is prepared from triazine 2a and intermediate 1e according to synthesis method 1 under the operating conditions described for example 1 (55% yield).

TLC silica gel 60 F 254 Merck, $CH_2Cl_2$-AcOEt: 80-20, Rf=05.

$^1$H NMR (DMSO-$d_6$) ppm: 3.24-3.28 (m, 1H), 4.07-4.10 (m, 2H), 4.28-4.32 (m, 2H), 4.43 (d, 2H, J=6 Hz), 7.32-7.36 (m, 1H), 7.51 (d, 1H, J=3 Hz), 7.66 (dd, 1H, J=3 Hz and J=9 Hz), 8.34 (d, 1H, J=3 Hz), 8.64 (d, 1H, J=3 Hz).

Example 42

3-[3-(2-Chloro-5-trifluoromethyl-phenoxy)-pyrrolidin-1-yl]-[1,2,4]triazine (42)

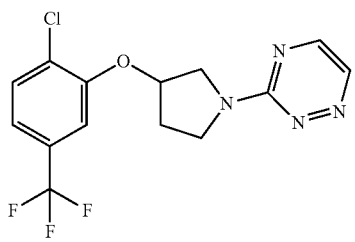 [SMILES: FC(F)(F)c1ccc(Cl)c(OC2CCN(c3nccnn3)C2)c1]

Compound 42 is prepared from 2-chloro-5-trifluoromethylphenol and intermediate 5d according to synthesis method 3 in toluene in the presence of DIAD, under the operating conditions described for example 8 (86% yield).

TLC silica gel 60 F 254 Merck, Cyclohexane-AcOEt: 60-40, Rf=0.4.

$^1$H NMR (DMSO-$d_6$) ppm: 2.21-2.42 (m, 2H), 3.60-3.90 (m, 4H), 5.48-5.49 (m, 1H), 7.33-7.37 (m, 1H), 7.63-7.68 (m, 2H), 8.33 (d, 1H, J=3 Hz), 8.63 (d, 1H, J=3 Hz).

Example 43

[(trans)-2-(2-Chloro-5-trifluoromethyl-phenoxymethyl)-cyclopropyl]-[1,2,4]triazin-3-yl-amine (43)

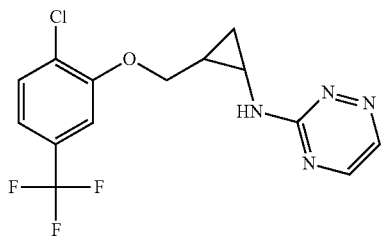 [SMILES: FC(F)(F)c1ccc(Cl)c(OCC2CC2Nc2nccnn2)c1]

Compound 43 is prepared from triazine 3 g and intermediate 1f according to synthesis method 1 under the operating conditions described for example 1 (8% yield).

TLC silica gel 60 F 254 Merck, CH$_2$Cl$_2$-AcOEt: 85-15, Rf=0.4.

$^1$H NMR (DMSO-$d_6$) ppm: 0.90-0.92 (m, 2H), 1.47-1.5 (m, 1H), 2.86-2.91 (m, 1H), 4.07-4.11 (m, 1H), 4.30-4.34 (m, 1H), 7.32 (d, 1H, J=9 Hz), 7.46 (d, 1H, J=3 Hz), 7.68 (d, 1H, J=9 Hz), 8.00-8.02 (s large, 1H), 8.27 (d, 1H, J=3 Hz), 8.63 (d, 1H, J=8 Hz).

MS (+APCI) m/z 345 (MH+)

Pharmacological Evaluation

Human SCD-1 enzyme activity using HepG2 cell microsomes after treating with inhibitory compounds (% inhibition):

Human hepatocarcinoma HepG2 cells (ATCC, HB-8065) are cultured to confluence and trypsinised. The cell pellet is taken up with 10 mM Tris (pH 7.4) sucrose (250 mM) DTT (1 mM) buffer and the cells are lysed by sonication. The microsomes are obtained after centrifugation at 10,000 g for 20 minutes at 4° C. followed by centrifugation of the supernatant at 100,000 g for 60 minutes at 4° C. The pellet is taken up with 10 mM Tris (pH 7.4) sucrose (250 mM) buffer at 4° C. and the microsomal proteins are assayed and stored at −196° C. (liquid nitrogen).

The enzyme reaction measures the conversion of stearic acid (C18:0 fatty acid) to oleic acid (C18:1 fatty acid) by SCD-1. The enzyme reaction is started by adding 125 µg of HepG2 cell microsomal fraction to tubes (total reaction volume of 500 µl) containing 62 µM of stearic acid (45 µM of stearic acid 17 µM of [$^{14}$C] stearic acid) in a 100 mM phosphate buffer (pH 7.16) with 7.2 mM of ATP, 0.54 mM of CoA, 6 mM of MgCl$_2$, 0.8 mM of NADH and the inhibitory compound or the vehicle (0.1% DMSO). The tubes are incubated for 20 minutes at 37° C. and the enzyme reaction is stopped by adding KOH (12%) and saponification for 30 minutes at 80° C. After acidification (3N HCl), the fatty acids are extracted twice with ethyl ether, evaporated in nitrogen before being taken up with methanol/dichloromethane (3:1). The reaction product (C18:1) is separated from the reaction substrate (C18:0) by HPLC (Perkin Elmer, C18 reverse phase column) coupled with an online radioactivity detector (FlowOne). The enzyme activity is calculated in picomoles of stearic acid converted into oleic acid per minute and per mg of protein. For each inhibitory compound, an IC$_{50}$ is determined in relation to the reference enzyme activity (0.1% DMSO vehicle). Sterculic acid is the reference inhibitory compound (Gomez F. E., Bauman D. E., Ntambi J. M., Fox B. G. Effects of sterculic acid on stearoyl-CoA desaturase in differentiating 3T3-L1 adipocytes. Biochem Biophys Res Commun. 300 316-326 (2003).

TABLE 5

| Human SCD-1 enzyme activity. | |
|---|---|
| Examples | HSCD-1 (HEPG2) IC$_{50}$ µM |
| Sterculic acid | 0.3 |
| 6 | 0.1-1 |
| 7 | 0.1-0.3 |
| 8 | 0.1-0.3 |
| 9 | 0.1-1 |
| 11 | 0.1 |
| 12 | 0.01-0.03 |
| 13 | 0.1-1 |
| 14 | 0.1-1 |
| 17 | 0.1 |
| 18 | 0.03 |
| 19 | 0.1-1 |
| 25 | 0.1 |
| 27 | 0.3 |
| 28 | 0.3-1 |
| 30 | 0.1 |
| 32 | 0.03-0.1 |
| 33 | 0.01-0.1 |
| 35 | 0.1-1 |
| 36 | 0.03 |
| 37 | 0.1-1 |
| 38 | 0.3-1 |
| 40 | 0.1-0.3 |
| 42 | 0.3-1 |

The results obtained demonstrated that the compounds having general formula (I) inhibit SCD-1 enzyme activity.

The compounds having general formula (I) may be used as SCD-1 enzyme inhibitors.

Topical application of SCD-1 inhibitory compounds to NMRI mice: reduction in number and size of sebaceous glands.

Experimental protocol: Crl:NMRI male mice (24-26 g) are shaved (2×2 cm$^2$ minimum) 2-3 days before the first application of molecules under test. To prevent potential oral intake of the molecules, the animals are accommodated individually.

The molecules are solubilised in the ethanol/propylene glycol (30/70, v/v) vehicle are a maximum concentration of 1%. 50 μl of each preparation (molecule under test, or vehicle) are applied twice daily for 5 consecutive days on the 2 cm² shaved area, with the cone of a pipette with a number of to-and-fro movements. At least 6 hours after the final application, the mice are euthanised, the skin samples are taken and fixed immediately to produce paraffin sections; a histomorphometric analysis after Haematoxylin/Eosin staining is carried out.

For each animal, at least 3 sections approximately 10 mm in length are read blind by 3 people, and the efficacy of the molecules on sebaceous gland atrophy is assessed quantitatively (number) and qualitatively (relative score, size). The duration of action, the reversibility of the effect are verified in the same way by modifying the application sequences.

TABLE 6 topical application of SCD-1 inhibitory compounds (NMRI mice): reduction in number and size of sebaceous glands.

| Examples | Concentration (%) | Treatment time | ↘ number of sebaceous glands (%) |
|---|---|---|---|
| 6 | 0.3 | 5 days | 79 |
| 7 | 0.3 | 5 days | 75 |
| 8 | 0.3 | 5 days | 95 |
| 9 | 0.3 | 5 days | 43 |
| 11 | 1 | 5 days | 45 |
| 12 | 0.3 | 5 days | 94 |
| 17 | 1 | 5 days | 97 |
| 40 | 0.1 | 5 days | 36 |

Cytotoxic activities with respect to human colon cancer cell lines (HCT-116):

HCT-116 tumour cells are inoculated in a 96-well plate in RPMI 1640 medium to which 5% foetal calf serum is added (100 μl/well, respectively at 1.5 10⁴ cells/ml). After 24 hours of incubation at 37° C. in an incubator at 5% $CO_2$, 11 μl of medium containing the compound under test at a concentration 10 times greater than the final concentration are added. The plates are incubated for a further 72 hours. Cell survival is evaluated by measuring the luminescence after releasing ATP in the medium using the cell lysis, luciferase and luciferin solutions contained in the ATP-lite-M™ kit as recommended by the manufacturer (Packard, Rungis, France). Each experimental condition was replicated at least three times independently with one well reading in sextuplet per dose interval.

The results demonstrate that the compounds according to the invention have powerful cytotoxic properties. The 50% inhibitory concentration ($EC_{50}$), the concentration of the compound inhibiting cell proliferation by 50%, is 60 nM for compound 12 and 230 nM for compound 17 on HCT-116 tumour line cells.

TABLE 7

Anti-proliferation activity of SCD-1 inhibitory compounds, in relation to the HTC116 human tumour line:

| Examples | $EC_{50}$ (μM) |
|---|---|
| 12 | 0.06 |
| 17 | 0.23 |

The invention claimed is:

1. A compound of general formula I

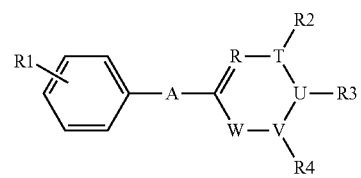

wherein

R1 is one or more substituents selected from the group consisting of trifluoromethyl, halogen, methyl, and nitro;

R is nitrogen; T-U is C=C; V is nitrogen; W is C=O; R2 is Cl or H; R3 is H; and R4 is Me;

A is

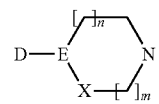

wherein n and m are both 1, X is —$CH_2$—, and E is —CH—, and D is oxygen;

or a pharmaceutically acceptable salt thereof.

2. A compound of general formula I according to claim 1, wherein $R_1$ is one or more substituents selected from the group consisting of F, Cl, and Br.

3. A compound of general formula I according to claim 1 selected from:

(1) 5-Chloro-3-[4-(2-chloro-phenoxy)-piperidin-1-yl]-1-methyl-1H-pyrazin-2-one, (2) 5-Chloro-1-methyl-3-[4-(2-trifluoromethyl-phenoxy)-piperidin-1-yl]-1H-pyrazin-2-one, (3) 5-Chloro-3-[4-(2-chloro-5-trifluoromethyl-phenoxy)-piperidin-1-yl]-1-methyl-1H-pyrazin-2-one, (4) 5-Chloro-1-methyl-3-(4-o-tolyloxy-piperidin-1-yl)-1H-pyrazin-2-one, (5) 1-Methyl-3-(4-o-tolyloxy-piperidin-1-yl)-1H-pyrazin-2-one, (6) 1-Methyl-3-[4-(2-trifluoromethyl-phenoxy)-piperidin-1-yl]-1H-pyrazin-2-one, and (7) 5-Chloro-3-[4-(2-chloro-5-fluoro-phenoxy)-piperidin-1-yl]-1-methyl-1H-pyrazin-2-one.

4. A pharmaceutical composition comprising as an active ingredient a compound of general formula I according to claim 1 and a suitable excipient.

5. The pharmaceutical composition according to claim 4, wherein the active ingredient and excipient are suitable for topical administration.

6. A process for preparing a compound of general formula I according to claim 1 which comprises condensation of a compound of general formula II

II

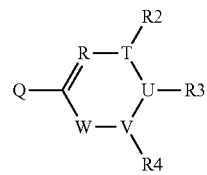

wherein R is nitrogen, Q is Cl; T-U is C═C; V is nitrogen; W is C═O; R2 is Cl or H; R3 is H; and R4 is Me;
the process comprising a step of condensing in the absence or presence of a base the compound of general formula II with a compound of general formula III or a hydrochloride salt thereof

III

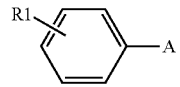

wherein A is

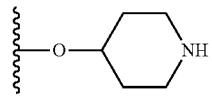

and R1 is defined as in general formula I.

7. The process of claim 6, wherein the condensation is carried out in the absence of a base in a tetrahydrofuran or ethanol solvent and in a microwave field; or in the presence of a triethylamine base in a n-butanol or acetonitrile solvent.

\* \* \* \* \*